United States Patent [19]

Udagawa et al.

[11] Patent Number: 5,994,388
[45] Date of Patent: Nov. 30, 1999

[54] CYTOCHALASIN AND ISOINDOLINONE DERIVATIVES AS INHIBITORS OF ANGIOGENESIS

[75] Inventors: Taturo Udagawa, Jamaica Plain; Robert J. D'Amato, Cambridge, both of Mass.; Jamshed H. Shah, Columbia, Md.

[73] Assignee: The Children's Medical Center Corporation, Boston, Mass.

[21] Appl. No.: 09/042,760

[22] Filed: Mar. 17, 1998

Related U.S. Application Data

[60] Provisional application No. 60/041,399, Mar. 18, 1997.

[51] Int. Cl.⁶ .................. A61K 31/40; C07D 209/46; C07D 209/58
[52] U.S. Cl. ................. 514/416; 514/417; 514/418; 514/419; 548/472; 548/473; 548/480; 548/481
[58] Field of Search ................... 514/416, 418; 548/472, 473, 481

[56] References Cited

U.S. PATENT DOCUMENTS 3,849,437 11/1974 Ousby et al. ........................ 260/325
5,593,990 1/1997 D'Amato ............................. 514/235.2

FOREIGN PATENT DOCUMENTS

| 58-036391 | 3/1983 | Japan . |
| WO 91/10424 | 7/1991 | WIPO . |
| WO 93/16716 | 9/1993 | WIPO . |
| WO 95/25543 | 9/1995 | WIPO . |
| WO 95/29242 | 11/1995 | WIPO . |

OTHER PUBLICATIONS

Algire, G.H. et al., "Vascular reactions of normal and malignant tumors in vivo. I. Vascular reactions of mice to wounds and to normal and neoplastic transplants", *J. Natl. Canc. Inst.*, vol. 6, pp. 73–85 (1945).

Angiolillo, A.l. et al., "Human interferon–inducible Protein 10 is a potent inhibitor of angiogenesis in vivo", *J. Exp. Med.*, vol. 182, pp. 155–162 (1995).

Brem, H. et al., "Intestinal chemotherapy with drug polymer implants for the treatment of recurrent gliomas", *J. Neurosurg.*, vol. 74, pp. 441–446 (1991).

Brenner, et al., "The Effects of Cytochalasins on Actin Polymerization and Actin ATPase Proved Insights into the Mechanism of Polymerization", *The J. Biol. Chem.*, vol. 255, No. 3, pp. 841–844 (1980).

Búchi, G. et al., "Structure of Cytochalasin E, a Toxic Metabolite of Aspergillus clavatus", *J.A.C.S.*, vol. 95, pp. 5423–5425 (1973).

Cao, Y. et al., "gro–β, α–C–X–C–Chemokine, Is an Angiogenesis Inhibitor That Suppresses the Growth of Lewis Lung Carcinoma in Mice", *J. Esp. Med.*, vol. 182, pp. 2069–2077 (1995).

Carter, S.B., "Effects of Cytochalasins on Mammalian Cells", *Nature*, vol. 213, No. 5073, pp. 261–264 (1967).

Chen, C. et al., "A A Strategy to Discover Circulating Angiogenesis Inhibitors Generated by Human Tumors", *Canc. Res.*, vol. 55, pp. 4230–4233 (1995).

Clapp, C. et al., "The 16–kilodalton N–terminal fragment of human prolactin is a potent inhibitor of angiogenesis", *Endocrinology*, vol. 133, pp. 1292–1299 (1993).

(List continued on next page.)

Primary Examiner—Johann Richter
Assistant Examiner—Jane C. Osweck
Attorney, Agent, or Firm—Jones & Askew

[57] ABSTRACT

The present invention relates to inhibition of angiogenesis and the treatment of diseases mediated by angiogenesis. Particularly, the invention relates to the inhibition of neovascularization and the treatment of cancer. The invention further relates to the use of cytochalasin derivatives for the inhibition of angiogenesis and the treatment of angiogenesis associated diseases. The invention also relates to new isoindolinone compounds, compositions containing them, and methods of inhibiting angiogenesis and treating angiogenesis associated diseases with the isoindolinone derivatives.

15 Claims, 5 Drawing Sheets

OTHER PUBLICATIONS

Dameron, K.M. et al., "Control of angiogenesis in fibroblasts by p53 regulation of thrombospondin–1", *Science*, vol. 265, pp. 1582–1584 (1994).

Flanagan, M.D. et al., "Cytochalasins Block Actin Filament Elongation by Binding to High Affinity Sites Associated with F–actin", *The J. Biol. Chem.*, vol. 255, No. 3, pp. 835–838 (1980).

Folkman, J., "Tumor angiogenesis and tissue factor", *Nature Med.*, vol. 2, pp. 167–168 (1996).

Folkman, J., "What is the Evidence that Tumors are Angiogenesis Dependent?", *J. Natl. Canc. Inst.*, vol. 82, pp. 4–6 (1990).

Folkman, J., "Angiogenesis in cancer, vascular, rheumatoid and other disease", *Nature Medicine*, vol. 1, No. 1, pp. 27–31 (1995).

Folkman, J., "Long–term culture of capillary endothelial cells", *Proc. Natl. Acad. Sci. USA* 76, pp. 5217–5221 (1979).

Folkman, J., "Induction of angiogenesis during the transition from hyperplasia to neoplasia", *Nature*, vol. 339, pp. 58–61 (1989).

Folkman, J., "Tumor Behavior in Isolated Perfused Organs In Vitro Growth and Metastases of Biopsy Material in Rabbit Thyroid and Canine Intestinal Segment", *Annals of Surgery*, vol. 164, No. 3, pp. 491–501 (1966).

Folkman, J., "Angiogenesis and Its Inhibitors", *Important Advances in Oncology*, J.B. Lippincott Company, pp. 42–62 (1985).

Folkman, J., "Tumor Angiogenesis Therapeutic Implications", *NE J. of Med.*, No. 18, pp. 1182–1186 (1971).

Gavrieli, Y. et al., "Identification of programmed cell death in situ via specific labeling of nuclear DNA fragmentation", *J. Cell Biol.*, vol. 119, pp. 493–501 (1992).

Gimbrone, M.A. et al., "Tumor Growth and Neovascularization An Experimental Model using the Rabbit Cornea", *J. Natl. Canc. Inst.*, vol. 52, No. 2, pp. 413–427 (1974).

Gimbrone, M.A. et al., "Tumor Dormancy in Vivo by Prevention of Neovascularization", *J. of Exper. Med.*, vol. 136, pp. 261–276 (1972).

Glinsukon, T. et al., "Acute and Subacture Toxicity of Cytochalasin E in the Rat", *Toxicology and Applied Pharmacology*, vol. 32, pp. 135–146 (1975).

Good, D.J. et al., "A tumor suppressor–dependent inhibitor of angiogenesis is immunologically and functionally indistinguishable from a fragment of thrombospondin", *Proc. Nat. Acad. Sci. USA*, vol. 87, pp. 6624–6628 (1990).

Grant, D.S. et al., "Scatter factor induces blood vessel formation in vivo", *Proc. Natl. Acad. Sci. USA*, vol. 99, pp. 1937–1941 (1993).

Grant, D.S. et al., "Two different laminin domains mediate the differentiation of human endothelial cells into capillary––like structures in vitro", *Cell*, vol. 58, pp. 933–943 (1989).

Gross, J.L. et al., "Modulation of Solid Tumor Growth in vivo by bFGF", *Proc. Amer. Assoc. Canc. Resh*, vol. 31, p. 79 (1990) (Abstract).

Gross, J.L. et al., "Increase capillary endothelial cell protease activity in response to angiogenic stimuli in vitro", *Proc. Natl. Acad. Sci. USA*, vol. 80, pp. 2623–2627 (1983).

Grumet, et al., "Reversal of Profilin Inhibition of Actin Polymerization In Vitro by Erthrocyte Cytochalasin–Binding Complexes and Cross–Linked Actin Nuclei", *Biochem. and Biophys. Res. Comm.*, vol. 92, No. 4, pp. 1327–1334 (1980).

Gupta, S.K. et al., "A potent inhibitor of endothelial cell proliferation is generated by proteolytic cleavage of the chemokine platelet factor 4", *Proc. Natl. Acad. Sci. USA*, vol. 92, pp. 7779–7803 (1995).

Holmgren, L. et al., "Dormancy of micrometastases Balanced proliferation and apoptosis in the presence of angiogenesis suppression", *Nature Med.*, vol. 1, No. 2, pp. 149–153 (1995).

Homandberg, G.A. et al., "Heparin–binding fragments of fibronectin are potent inhibitors of endothelial cell growth", *Am. J. Path.*, vol. 120, pp. 327–332 (1985).

Hori, A. et al., "Suppression of Solid tumor Growth by Immunoneutralizing Monoclonal Antibody against Human Basic Fibroblast Growth Factor", *Canc. Res.*, vol. 51, pp. 6180–6184 (1991).

Ingber, D. et al., "Synthetic analogues of fumagillin that inhibit angiogenesis and suppress tumor growth", *Nature*, vol. 348, pp. 555–557 (1990).

Kajimoto, T. et al., "Nuclear Magnetic Resonance Studies of Cytochalasin E and Its Decomposition Product", *Chem. & Pharm. Bull.*, vol. 37, No. 8, pp. 2212–2213 (1989).

Kandel, J. et al., "Neovascularization is Associated with a Switch to the Expert of bFGF in the Multistep Development of Fibrosarcoma", *Cell*, vol. 66, pp. 1095–1104 (1991).

Kim, K.J. et al., "Inhibition of vascular endothelial growth factor–induced angiogenesis suppresses tumor growth in vivo", *Nature*, vol. 362, pp. 841–844 (1993).

Knighton, D. et al., "Avascular and Vascular Phases of Tumor Growth in the Chick Embryo", *Br. J. Cancer*, vol. 35, pp. 347–356 (1977).

Lein, W. M. et al., "The blood supply of experimental liver metastases. II. A Microcirculatory study of the normal and tumor vessels of the liver with the use of perfused silicone rubber", *Surgery*, vol. 68, No. 2, pp. 334–340 (1970).

Lerch et al., "Localization of Individual Lysine–Binding Regions in Human Plasminogen and Investigations on Their Complex–Forming Properties", *European Journal of Biochemistry*, vol. 107, No. 1, pp. 7–13 (1980).

Lin, et al., "On the Mechanism for Inactivation of Cytochalasin Binding Activity Associated with F–Actin and Spectrin–Band 4.1–Actin Complex by Sulfhydryl Reagents", *Biochem. and Biophys. Res. Comm.*, vol. 122, No. 1, pp. 244–251 (1984).

Maione, T.E. et al., "Inhibition of Angiogenesis by Recombinant Hum,an Platelet Factor–4 and Related Peptiddes", *Science*, vol. 247, pp. 77–79 (1990).

McPherson, et al., "Inhibition of DNA Synthesis in Adrenocortical Cells by Cytochalasin B", *The Journal of Cell Biology*, vol. 86, pp. 129–134 (1980).

Millauer, B. et al., "Glioblastoma growth inhibited in vivo by a dominant–negative Flk–1 mutant", *Nature*, vol. 367, pp. 576–579 (1994).

Mookerjee, et al., "Cytochalasin Effects on Lymphocytes", *The J. Biol. Chem.*, vol. 256, No. 3, pp. 1291–1300 (1981).

Moses, M.A. et al., "Identification of an Inhibitor of Neovascularization from Cartilage", *Science*, vol. 248 (1990).

Muragaki, Y. et al., "Mouse col 18a1 is expressed in a tissue–specific manner as three alternative variants and is localized in basement membrane zones", *Proc. Natl. Acad. Sci. USA*, vol. 92, pp. 8763–8767 (1995).

Muthukkaruppan, VR., "Angiogenesis in the Mouse Cornea", *Science*, vol. 205, pp. 1416–1418 (1979).

Nelson, J.A. et al., "Murine epidermal growth factor (EGF) fragment (33–42) inhibits both EGF–and laminin–dependent endothelial cell motility and angiogenesis", *Canc. Res.*, vol. 55, pp. 3772–3776 (1995).

Nguyen, M. et al., "Quantitation of Angiogenesis and Antiangiogenesis in the Chick Embryo Chorioallantioc Membrane", *Microvascular Research*, vol. 47, pp. 31–49 (1994).

Nguyen, M. et al., "Elevated Levels of the Angiogenic Peptide Basic Fibroblast Growth Factor in Urine of Bladder Cancer Patients", *J. of Natl. Canc. Inst.*, vol. 85, No. 3, pp. 241–242 (1993).

Obeso, J. et al., Methods in Laboratory Investigation/A Hemangioendothelioma–Derived Cell Line Its Use as a Model for the Study of Endothelial Cell Biology, *Lab Invest.*, vol. 63, No. 2, p. 159 (1990).

Oikawa, T. et al., "Eponemycin A Novel Antibiotic is a Highly Powerful Angiogenesis Inhibitor", *Biochem. & Biophys. Res. Comm.*, vol. 181, No. 3, pp. 1070–1076 (1991).

O'Reilly et al., "Angiostatin: A Circulating Endothelial Cell Inhibitor That Suppresses Angiogenesis and Tumor Growth", *Cold Spring Harbor Symposia on Quantitative Biology*, vol. LIX, pp. 471–482 (1994).

O'Reilly et al., "Angiostatin induces and sustains dormancy of human primary tumors in mice", *Nature Med.*, vol. 2, No. 6, pp. 689–692 (1996).

O'Reilly et al., "Angiostatin A Novel Angiogenesis Inhibitor that Mediates the Suppression of Metastases by a Lewis Lung Carcinoma", *Cell*, vol. 79, pp. 315–328 (1994).

O'Reilly et al., "Endogenous Inhibitors of Angiogenesis", *Proc. Am. Assoc. Canc. Res.*, vol. 37, p. 669 (1996) (abstract).

O'Reilly et al., "The suppressionof Tumor Metastases by a Primary Tumor", *Surgical Forum*, vol. XLIV, pp. 474–476 (1993).

Parangi, S. et al., "Antiangiogenic therapy of transgenic mice impairs de novo tumor growth", *Proc. Natl. Acad. Sci. USA*, vol. 93, pp. 2002–2007 (1996).

Passaniti, A. et al., "Methods in Laboratory Investigation/A Simple, Quantitative Method for Assessing Angiogenesis and Antiangiogenesis Agents Using Reconstituted Basement Membrane, Heparin, and Fibroblast Growth Factor",*Lab. Invest.*, vol. 67, no. 4, pp. 519–528 (1992).

Rastinejad, F. et al., "Regulation of the activity of a new inhibitor of angiogenesis by a cancer suppressor gene", *Cell*, vol. 56, pp. 345–355 (1989).

Rothweiler et al., "Isolation and Structure of Phomin", *Experientia*, vol. 22, No. 11, pp. 750–752 (1966).

Sage, E.H. et al., "Inhibition of Endothelial Cell Proliferation by SPARC is Mediated through $Ca^{2+}$–Binding EF–Hand Sequence", *J. Cell. Biochem.*, vol. 57, pp. 127–140 (1995).

Sakamoto, N. et al., "Inhibition of angiogenesis and tumor growth by a synthetic laminin peptide, CDPGYIG-SR–$NH_2$", *Canc. Res.*, vol. 51, pp. 903–906 (1991).

Srivastava, A. et al., "The Prognostic Significance of Tumorascularity in Intermediate–Thickness (0.76–4.0mm Thick) Skin Melanoma", *Am. J. of Path.*, vol. 133, No. 2, pp. 419–424 (1988).

Stieter, R.M. et al., Interferonγ–inducible protein 10 (IP–10), a member of the C–X–C chemokine family, is an inhibitor of angiogenesis. *Biochem. Biophys. Res. Comm.*, vol. 210, pp. 51–57 (1995).

Teicher, B.A. et al., "Potentiation of cytotoxic cancer therapies by TNP–470 alone and with other antiangiogenic agents", *Int. J. Canc.*, vol. 57, pp. 1–6 (1994).

Tolsma, S.S. et al., "Peptides derived from two separate domains of the matrix protein thrombospondin–1 have antiangiogenic activity", *J. Cell Biol.*, vol. 122, pp. 497–511 (1993).

Tirawatanapong, et al., "Alteration of Vascular Permeability Due to Cytochalasin E", *Toxicology and Applied Pharmacology*, vol. 52, pp. 209–213 (1980).

Van Meir, E. et al., "Release fo an inhibitor of angiogenesis upon induction of wild type p53 expression in glioblastoma cells", *Nature Genetics*, vol. 8, pp. 171–176 (1994).

Voest, E. E. et al., "Inhibition of Angiogenesis in Vivo by Interleukin 12", *J. Natl. Canc. Inst.*, vol. 87, pp. 581–586 (1995).

Weidner, N. et al., "Tumor Angiogenesis: A New Significant and Independent Prognostic Indicator in Early–Stage Breast Carcinoma", *J. Natl. Canc. Inst.*, ovl. 84, pp. 1875–1887 (1992).

Wiedner, N. et al., "Tumor Angiogenesis Correlates with Metastasis in Invasive Prostate Carcinoma", *Am. J. Path.*, vol. 143, No. 2, pp. 401–409 (1993).

Weidner, N. et al., "Tumor Angiogenesis and Metastasis—Correlation in Invasive Breast Carcinoma", *NE J. of Med.*, vol. 324, No. 1, pp. 1–8 (1991).

Grant, et al., "Intracellular Mechanisms Invovled in Basement Membrane Induced Blood Vessel Differentiation in Vitro", *In Vitro Cell Dev. Biol.*, vol. 27A(4), pp. 327–336 (1991) (Abstract Only).

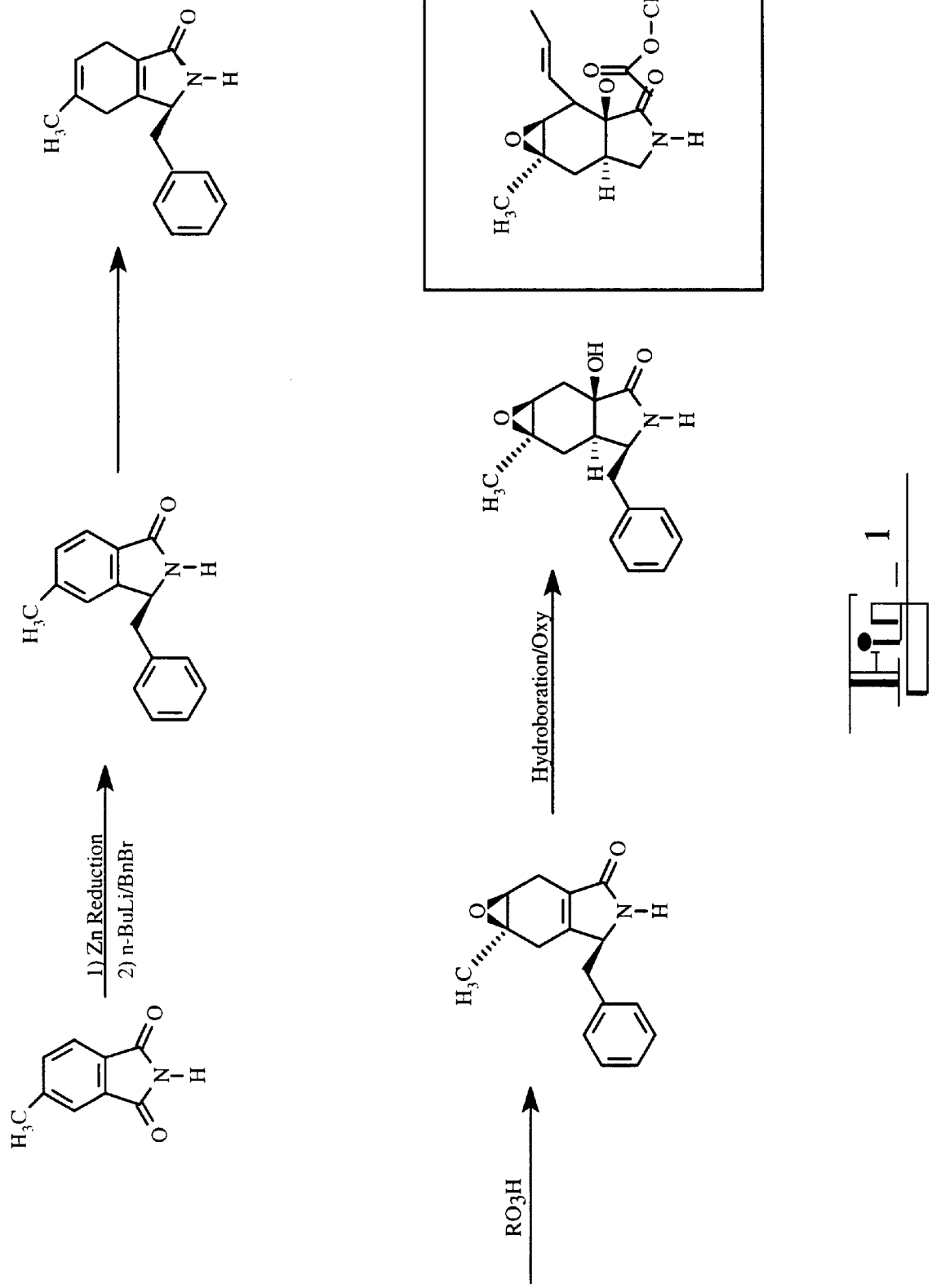

CYTOCHALASIN AND ISOINDOLINONE DERIVATIVES AS INHIBITORS OF ANGIOGENESIS

RELATED APPLICATIONS

This application claims priority to U.S. provisional patent application Ser. No. 60/041,399.

FIELD OF THE INVENTION

The invention relates generally to the inhibition of angiogenesis. More particularly, the invention relates to the treatment of angiogenesis dependent and angiogenesis associated diseases, such as neovascularization and cancer. Further, the invention relates to the use of cytochalasin derivatives and isoindolinone derivatives.

BACKGROUND OF THE INVENTION

Angiogenesis is the generation of new blood vessels into a tissue or organ. Under normal physiological conditions, humans and animals undergo angiogenesis only in very specific restricted situations. For example, angiogenesis is normally observed in wound healing, fetal and embryonal development, and formation of the corpus luteum, endometrium and placenta.

Angiogenesis is controlled through a highly regulated system of angiogenic stimulators and inhibitors. The control of angiogenesis has been found to be altered in certain disease states and, in many cases, pathological damage associated with the diseases related to uncontrolled angiogenesis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. Endothelial cells, lining the lumen of blood vessels then protrude through the basement membrane. Angiogenic stimulants induce the endothelial cells to migrate through the eroded basement membrane. The migrating cells form a "sprout" off the parent blood vessel where the endothelial cells undergo mitosis and proliferate. The endothelial sprouts merge with each other to form capillary loops, creating a new blood vessel.

Persistent, unregulated angiogenesis occurs in a multiplicity of disease states, tumor metastases, and abnormal growth by endothelial cells. The diverse pathological disease states in which unregulated angiogenesis is present have been grouped together as angiogenic-dependent or angiogenic-associated diseases.

One example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of choroidal capillaries through defect in Bruch's membrane with proliferation of fibrovascular tissue beneath the retinal pigment epithelium. Angiogenic damage is also associated with diabetic retinopathy, retinopathy of prematurity, corneal graph rejection, neovascular glaucoma, and retrolental fibroplasia. Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens disease, acne rosacea, phylectenulosis, syphilis, Mycobacteria infections, lipid degeneration, chemical burns, bacterial ulcers, fungal ulcers, Herpes simplex infection, Herpes zoster infections, protozoan infections, Kaposi's sarcoma, Mooren's ulcer, Terrien's marginal degeneration, marginal keratolysis, rheumatoid arthritis, systemic lupus, polyarteritis, trauma, Wegener's sarcoidosis, scleritis, Stevens-Johnson's disease, pemphigoid, and radial keratotomy.

Diseases associated with retinal/choroidal neovascularization include, but are not limited to, diabetic retinopathy, macular degeneration, sickle cell anemia, sarcoidosis, syphilis, pseudoxanthoma elasticum, Paget's disease, vein occlusion, artery occlusion, carotid obstructive disease, chronic uveitis/vitritis, Mycobacteria infections, lyme's disease, systemic lupus erythematosis, retinopathy of prematurity, Eale's disease, Behcet's disease, infections causing a retinitis or choroiditis, presumed ocular histoplasmosis, Best's disease, myopia, optic pits, Stargardt's disease, pars planitis, chronic retinal detachment, hyperviscosity syndromes, toxoplasmosis, trauma and post-laser complications. Other eye-related diseases include, but are not limited to, diseases associated with rubeosis (neovascularization of the angle) and diseases caused by the abnormal proliferation of fibrovascular or fibrous tissue, including all forms of prolific vitreoretinopathy.

Another angiogenesis associated disease is rheumatoid arthritis. The blood vessels in the synovial lining of the joints undergo angiogenesis. In addition to forming new vascular networks, the endothelial cells release factors and reactive oxygen species that lead to pannus growth and cartilage destruction. Angiogenesis may also play a role in osteoarthritis. The activation of the chondrocytes by angiogenic-related factors contributes to the destruction of the joint. At a later stage, the angiogenic factors promote new bone growth. Therapeutic intervention that prevents the bone destruction could halt the progress of the disease and provide relief for persons suffering with arthritis.

Chronic inflammation may also involve pathological angiogenesis. Such diseases as ulcerative colitis and Crohn's disease show histological changes with the ingrowth of new blood vessels and the inflamed tissues. Bartonelosis, a bacterial infection found in South America, can result in a chronic stage that is characterized by proliferation of vascular endothelial cells. Another pathological role associated with angiogenesis is found in atherosclerosis. The plaques formed within the lumen of blood vessels have been shown to have angiogenic stimulatory activity.

The hypothesis that tumor growth is angiogenesis-dependent was first proposed in 1971. (Folkman, *New Eng. J Med.*, 285:1182–86 (1971)) In its simplest terms, this hyposthesis states: "Once tumor 'take' has occurred, every increase in tumor cell population must be preceded by an increase in new capillaries converging on the tumor." Tumor 'take' is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire, et al., *J. Nat. Cancer Inst.*, 6:73–85 (1945)).

(2) Tumors grown in isolated perfused organs where blood vessels do not proliferate are limited to 1–2 mm$^3$ but expand rapidly to >1000 times this volume when they are transplanted to mice and become neovascularized. (Folkman, et al., *Annals of Surgery*, 164:491–502 (1966)).

(3) Tumor growth in the avascular cornea proceeds slowly and at a linear rate, but switches to exponential growth after neovascularization. (Gimbrone, Jr., et al., *J. Nat. Cancer Inst.*, 52:421–27 (1974)).

(4) Tumors suspended in the aqueous fluid of the anterior chamber of the rabbit eye remain viable, avascular, and limited in size to <1 mm$^3$. Once they are implanted on the iris vascular bed, they become neovascularized and grow rapidly, reaching 16,000 times their original volume within 2 weeks. (Gimbrone, Jr., et al., *J. Exp. Med.*, 136:261–76).

(5) When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton, *British J. Cancer*, 35:347–56 (1977)).

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien, et al., *Surgery*, 68:334–40 (1970)).

(7) In transgenic mice which develop carcinomas in the beta cells of the pancreatic islets, pre-vascular hyperplastic islets are limited in size to <1 mm. At 6–7 weeks of age, 4–10% of the islets become neovascularized, and from these islets arise large vascularized tumors of more than 1000 times the volume of the pre-vascular islets. (Folkman, et al., *Nature*, 339:58–61 (1989)).

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim, et al., *Nature* 362:841–44 (1993)).

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori, et al., *Cancer Res.*, 51:6180–84 (1991)).

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumors cells in vitro. (Gross, et al., *Proc. Am. Assoc. Cancer Res.*, 31:79 (1990)).

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber, et al., *Nature*, 48:555–57 (1990)). There is also indirect clinical evidence that tumor growth is angiogenesis dependent.

(12) Human retinoblastomas that are metastatic to the vitreous develop into avascular spheroids which are restricted to less than 1 mm$^3$ despite the fact that they are viable and incorporate $^3$H-thymidine (when removed from an enucleated eye and analyzed in vitro).

(13) Carcinoma of the ovary metastasizes to the peritoneal membrane as tiny avascular white seeds (1–3 mm$^3$). These implants rarely grow larger until one or more of them becomes neovascularized.

(14) Intensity of neovascularization in breast cancer (Weidner, et al., *New Eng. J. Med.*, 324:1–8 (1991); Weidner, et al., *J Nat. Cancer Inst.*, 84:1875–87 (1992)) and in prostate cancer (Weidner, et al., *Am. J Pathol.*, 143(2):401–09 (1993)) correlates highly with risk of future metastasis.

(15) Metastasis from human cutaneous melanoma is rare prior to neovascularization. The onset of neovascularization leads to increased thickness of the lesion and an increased risk of metastasis. (Srivastava, et al., *Am. J. Pathol.*, 133:419–23 (1988)).

(16) In bladder cancer, the urinary level of an angiogenic protein, bFGF, is a more sensitive indicator of status and extent of disease than is cytology. (Nguyen, et al., *J. Nat. Cancer Inst.*, 85:241–42 (1993)).

Thus, it is clear that angiogenesis plays a major role in the metastasis of cancer. If this angiogenic activity could be repressed or eliminated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

Angiogenesis has been associated with a number of different types of cancer, including solid tumors and blood-borne tumors. Solid tumors with which angiogenesis has been associated include, but are not limited to, rhabdomyosarcomas, retinoblastoma, Ewing's sarcoma, neuroblastoma, and osteosarcoma. Angiogenesis is also associated with blood-borne tumors, such as leukemias, any of various acute or chronic neoplastic diseases of the bone marrow in which unrestrained proliferation of white blood cells occurs, usually accompanied by anemia, impaired blood clotting, and enlargement of the lymph nodes, liver and spleen. It is believed to that angiogenesis plays a role in the abnormalities in the bone marrow that give rise to leukmia-like tumors.

One of the most frequent angiogenic diseases of childhood is the hemangioma. Hemangioma is a tumor composed of newly-formed blood vessels. In most cases the tumors are benign and regress without intervention. In more severe cases, the tumors progress to large cavernous and infiltrative forms and create clinical complications. Systemic forms of hemangiomas, hemangiomatoses, have a high mortality rate. Therapy-resistant hemangiomas exist that cannot be treated with therapeutics currently in use.

Angiogenesis is also responsible for damage found in heredity diseases such as Osler-Weber-Rendu disease, or heredity hemorrhagic telangiectasia. This is an inherited disease characterized by multiple small angiomas, tumors of blood or lymph vessels. The angiomas are found in the skin and mucous membranes, often accompanied by epitaxis (nose bleeds) or gastrointestinal bleeding and sometimes with pulmonary or hepatitic arteriovenous fistula.

What is needed, therefore, is a composition and method which can inhibit angiogenesis. What is also needed is a composition and method which can inhibit the unwanted growth of blood vessels, especially in tumors.

Angiogenesis is also involved in normal physiological processes, such as reproduction and wound healing. Angiogenesis is an important step in ovulation and also in implantation of the blastula after fertilization. Prevention of angiogenesis could be used to induce amenorrhea, to block ovulation, or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Several compounds have been used to inhibit angiogenesis. Taylor, et al (*Nature*, 297:307 (1982)) have used protamine to inhibit angiogenesis. The toxicity of protamine limits its practical use as a therapeutic. Folkman, et al. (*Science*, 221:719 (1983), and U.S. Pat. Nos. 5,001,116 and 4,994,443) have disclosed the use of heparin and steroids to control angiogenesis. Steroids, such as tetrahydrocortisol, which lack gluccocorticoid and mineralocorticoid activity, have been found to be angiogenic inhibitors.

Other factors found endogenously in animals, such as a 4 kDa glycoprotein from bovine vitreous humor and a cartilage derived factor, have been used to inhibit angiogenesis. Cellular factors, such as interferon, inhibit angiogenesis. For example, interferon alpha or human interferon beta have been shown to inhibit tumor-induced angiogenesis in mouse dermis stimulated by human neoplastic cells. Interferon beta is also a potent inhibitor of angiogenesis induced by allogeneic spleen cells. (Sidky, et al., *Cancer Res.*, 47:5155–61 (1987)). Human recombinant interferon (alpha/A) was reported to be successfully used in the treatment of pulmonary hemangiomatosis, an angiogenesis-induced disease. (White, et al., *New Eng. J. Med.*, 320:1197–1200 (1989)).

Other agents which have been used to inhibit angiogenesis include ascorbic acid ethers and related compounds. (Japanese Kokai Tokkyo Koho No. 58-13 (1978)). Sulfated polysaccharide DS 4152 also inhibits angiogenesis. (Japanese Kokai Tokkyo Koho No. 63-119500).

The above compounds lack adequate potency or are too toxic for practical use. Thus, methods and compositions are needed that are easily administered and capable of inhibiting angiogenesis.

Cytochalasins are secondary metabolites of mold and fungi. They are classified into two groups, Ascomycotina and Deuteromycotina. Four other types of compounds are associated with cytochalasins due to their similarity in chemical structure and activity. These are Chaetoglobosins (Chaetomium sp.), Aspochalasins (Aspergillus sp.), Zygosporins (Zygosporum sp.), and Phomins (Phoma sp.). The cytochalasins include fifteen compounds named from A to M (e.g., cytochalasin A); the chaetoglobulins include 13 compounds named from A to K; the aspochalasins include four compounds named from A to D. There are five zygosporins and five phomins which are each associated with a different cytochalasin. There are also many known derivatives of each of the various cytochalasins, for example, 17-hydroxycytochalasins, 19,20-dihydrocytochalasins, and substituted cytochalasins. (*Cytochalasins: Biochemical and Aspects*, S. W. Tannenbaum, ed., North Holland Pub. Co., 15, 18, 320 (1978)). Reduction products of cytochalasins are also known. (Steyn, et al., *J. Chem. Soc., Perkin Trans* 1, 541–44 (1982)).

Structurally, cytochalasins contain a highly substituted hydrogenated isoindolinone ring system, called cytochalasan, to which a macrocyclic ring is fused. The macrocyclic ring varies from 11 to 14 atoms in size and is either a carbocyclic ring, a lactone, or a cyclic carbonate. The major structural differences amongst cytochalasins, chaetoglobosins, and aspochalasins are a phenyl ring, indolyl group, and isopropyl group respectively at the C-10 position.

Cytochalasins can be produced by fermentation. For example, Adridge, et al. (*J. Chem. Soc.*, C: 1667–76 (1967)) have suggested that cytochalasins A and B can be produced from fermentation on Raulin's medium. Other cytochalasins can be produced from KC medium with shredded wheat. (Springer, et al., *Tet. Lett.*, 1355–58 (1976); Zabel, et al., *Appl. Environ. Microbiol.*, 37:208–17 (1979); Cutler, et al., *J. Agric. Food Chem.*, 28: 139–42 (1980); Probst and Tamm, *Helv. Chem. Acta.*, 64(7): 2056–64 (1981)) Some cytochalasins have also been produced by shake culture using glucose, soybean cake, $KH_2PO_4$ and corn steep liquor medium. (Sekita, et al., *Tet. Lett.*, 1351–54 (1976)).

Several biosynthetic pathways have been used to generate cytochalasins. For example, cytochalasin D has been synthesized from *Zygosporium masonii* using $^{13}C$ and $^{14}C$ labelled sodium acetate, propionate, and malonate. This process uses the acetate malonate pathway to generate a C-16 polyketide moiety in which eight acetate units are linked head to tail. The polyketide is then incorporated with L-phenylalanine, followed by condensation to form a 5-membered lactum. The lactum undergoes reduction and dehydration, followed by Diels-Alder cyclization to give a cytochalasin. The carbonate and lactone ring system can be formed, for example, by Bayer-Villiger type oxidation of the macrocycle. (Binder, et al., *J. Chem. Soc. Perkin Trans.*, 1: 1146–47 (1973); Lebet and Tamm, *Helv. Chem. Acta.*, 57: 1785–1801 (1974); Vederas and Tamm, *Helv. Chim. Acta.*, 59: 558–66 (1976); Vederas, et al., *Helv. Chim. Acta*, 58, 1886–98 (1975); and Wyss, et al., *Helv. Chim. Acta*, 63: 1538–41 (1980)).

Another method for producing cytochalasins is Kolbe coupling. For example, cytochalasin B has been synthesized from (+) citronellol and (+) malic acid derivatives. (Stork, et al., *J. Am. Chem. Soc.*, 100: 7775–77 (1978)). Vedejs and Reid have also described the synthesis of zygosporin G. (Vedejs and Reid, *J. Am. Chem. Soc.*, 106: 4617–18 (1984)). Additionally, a number of researchers have described the partial synthesis of cytochalasins, such as formation of the isoindolinone unit and cycloundecaconone. (Kim and Weinreb, *Tet. Lett.*, 20: 576–82 (1979); Owen and Raphael, *J. Chem. Soc. Perkin Trans.*, 1: 1504–07 (1978).

Cytochalasins are capable of eliciting and moderating several cellular activities, such as enucleation of cells, inhibition of cell motility, and interference with cytoplasmic cleavage. Cytochalasins also affect the transportation of certain biochemicals across the cell memberane.

In a study by Carter (*Nature*, 293: 302–5 (1967)), cytochalasins displaced the nuclei from the cytoplasm of cultured L929 cells without affecting cell variability. This response is dose and time dependent. At lower doses and incubation times, the effect can be reversed by transferring the cells to medium which does not contain cytochalasin. At higher doses and incubatoin times, the L929 cells undergo enucleation.

The mechanism for enucleation is not known; however, several hypotheses have been proposed. Poste and Lyon (*Cytochalasins: Biochemical and Cell Biological Aspects*, S. W. Tannenbaum, ed., 161–89 (1978)) suggest that enucleation occurs due to depolymerization of cortical microfilaments, along with an increase in hydrostatic pressure in the cytoplasm. Bhisey, et al. (*Exp. Cell Res.*, 95: 376–84 (1975)) suggest that enucleation occurs due to active contraction of cytoplasm. Their studies showed a number of morphological changes in cell structure when the cells were treated with cytochalasin B which indicates that enucleation is an active, rather than passive, phenomenon.

Cytochalasins exhibit a number of cytotoxic and teratogenetic effects. These include mutinucleation, inhibition of fertilization, teratogenic effects, and chromosomal abnormalities. Cytochalasins have been shown to depolymerize microfilaments in the contractile ring during telophase, resulting in nuclear division not followed by cytokinesis. Thus, multimucleated cells are produced. (Aubin, et al., *Exp. Cell Res.*, 136: 63–79 (1981)). The affects of cytochalasin on microfilaments also results in inhibition of DNA synthesis (O'Neil, *J. Cell Physio.*, 101: 201–17 (1980)) and inhbition of cytokinesis. (*Cytochalasins: Biochemical and Cell Biological Aspects*, S. W. Tannenbaum, ed., North Holland Pub. Co., 217–55 (1978); O'Neil and Renzetti, *Cancer Res.*, 43: 521–28 (1983); Maness and Walsh, *Cell*, 30: 253–62 (1982)). Further, inhibition of microfilaments inhibits fertilization of eggs (Brunhouse, et al., *Biol. Bull.*, 143: 456 (1982)), formation of fertilization cone, and elongation of micro villi. (Longo, *Dev. Biol.*, 67: 249–65 (1978); Longo, *Dev. Biol.*, 74: 422–33 (1980); Schatten and Schatten, *Dev. Biol.*, 78: 435–49 (1980); Byrd, *J. Cell Biol.*, 75: 267 (1977); Eddy and Shapiro, *J. Cell Biol.*, 71: 35–48 (1976)).

Cytochalasins also inhibit cell adhesion due to changes in the cell surface. In part these changes are due to changes in the microfilaments that affect electrical properties in the cell membrane. (Vaidyasagar, Advances in cytochalasins, Indian Drugs Res. Assoc., 149–57 (1986)). Fluctuations in these electrical properties cause morphological changes in the cell membrane. (Wadekar, et al., *Exp. Cell Biol.*, 48: 155–66 (1980); Ghaskadbi and Mulherkar, *Exp. Cell Biol.*, 50: 155–61 (1982)). These changes are also due in part to the action of the cytochalasins on cell surface macromolecules. This action inhibits cell growth and motility. These changes are also due to inhibition in the synthesis of mucopolysaccharide glycoprotein complex which binds cells together. (Sangar and Holtzer, *Am. J. Anat.*, 135: 293–98 (1972); Burnside and Manasek, *Dev. Biol.*, 27: 443–44 (1972); Brachet and Tencer, *Acta Embryol. Exp.*, 1: 83–104 (1973)). Additionally, studies with cytochalasin H show that it produces disaggregation of cells resulting in inhibition of morphogenetic movements.

The teratogenic effects of cytochalasins have been studied in several different models, such as amphibians, mice, and chick embryo explants. In chick embryos cytochalasins have been shown to interfere with neural tube closure, cardiac looping, inhibition of primary morphogenesis of heart neural tube closure, interkinetic nuclear migration and segment formation, disaggregation of cells, microencephaly, exencephaly, and shortening of body axis. Although the exact mechanisms causing these teratogenic effects are not known, one proposed mechanism is through the inhibition of microtubules that are required for early differentiation in chick embryonic sensory neurons. (*Cytochalasins: Biochemical and Cell Biological Aspects*, S. W. Tannenbaum, ed., North Holland Pub. Co., 113–42 (1978); Austin, et al., *Teratology*, 25: 11–18 (1982); Karfunkel, *J. Exp. Zool.*, 181: 289–302 (1972); Greenway, et al., *Proc. Soc. Exp. Biol. Med.*, 155: 239–42 (1977); Peter, et al., *Brain Res.*, 42 (1): 73–81 (1987); Messier and Auclair, *Dev. Biol.*, 36: 218–23 (1974)).

Other teratogenic effects have been demonstrated in human lymphocytes, including chromosonal abnormalities. Some of the chromosomal abnormalities associated with cytochalasins include premature chromosomal condensation, extreme extension of chromosomes, ladder-like secondary constriction of chromosomes associated with bi- and multi-nucleated cells.

The cytoskeleton of the cell contains microfilaments consisting mainly of actin. Cytochalasins affect cell motility and cell shape by altering these microfilaments. In normal cells, they cause a shortening and segmentation of localized masses of actin filaments. In cell morphology studies, a generalized cell contraction was observed. Contractile proteins form actin cables condensed into masses at the base of zeiotic blebs.

Cytochalasins inhibit polymerization of actin filaments from actin nuclei by inhibiting filament elongation by blocking their growing barbed end. (Flanagan and Lin, *J. Biol. Chem.*, 255: 835–38 (1981); Lin, et al., *Biochem., Biophys. Res. Com.*, 122: 244–51 (1981); Casella, et al., *Nature*, 293: 302–5 (1981)). Several mechanisms for blocking actin filaments have been proposed. One proposed mechanism is that cytochalasins bind to the growing end of actin filaments and stimulate actin ATPase leading to depolymerization of actin filaments. (Brenner and Korn, *J. Biol. Chem.*, 254: 9982–85 (1981)). Another proposed mechanism is that cytochalasins cut actin filaments into small pieces. (Morris and Tanenbaum, *Nature*, 287: 637–39 (1980)). A third proposed mechanism is that depolymerization and growth of actin filaments is inhibited by capping the filaments with cytochalasins, resulting in contraction of the cytoplasmic network and, ultimately, expulsion of the nuclei from the cell.

Cytochalasins affect the transportion of certain molecules across cell membranes. These molecules include hexose, amino acids, and various nucleosides. This transport is neither competitive nor noncompetitive (Glinsukon, et al., *Toxicol. Lett.*, 15: 341–48 (1983); Toskulkao, et al., *Nutr. Res. Int.*, 27: 611–18 (1983)) and is mediated by a number of functional carriers on the cell membrane. (Yamada, et al., *J Biol. Chem.*, 258: 9786–92 (1982)).

SUMMARY OF THE INVENTION

In accordance with the present invention, compositions and methods are provided that are effective for modulating angiogenesis and inhibiting unwanted angiogenesis, especially angiogenesis related to neovascularization and tumor growth. The present invention comprises the modulation and inhibition of angiogenesis with cytochalasin derivatives. The term "cytochalasin derivative" means any compound having the cytochalasan structure, including, but not limited to, Cytochalasins, Chaetoglobulins, Aspochalasins, Zygosporins, and Phomins. Preferred cytochalasin derivatives are cytochalasins and chaetoglobosins having an epoxy group, a carbonate group, or both, for example, cytochalasin E. Especially preferred compounds are cytochalasins A, B, E, F, H, Q, and R; chaetoglobosins A, C, F, and K; rosellichalasin; and derivatives thereof.

The present invention also comprises new isoindolinone derivatives having an epoxide group, a carbonate group, or both. The invention also comprises compositions containing these isoindolinone derivatives, and methods for modulating angiogenesis and inhibiting unwanted angiogenesis with the compounds and compositions.

The present invention provides methods and compositions for treating diseases and processes mediated by undesired or uncontrolled angiogenesis by administering to a human or animal a composition comprising a cytochalasin derivative or an isoindolinone derivative in a dosage sufficient to inhibit angiogenesis. The present invention is particularly useful for treating neovascularization and tumors. Additionally, administration of a cytochalasin derivative or an isoindolinone derivative to a human or animal with prevascularized metastasized tumors will prevent the growth or expansion of those tumors.

Accordingly, it is an object of the present invention to provide a composition comprising one or more cytochalasin derivatives.

It is another object of the present invention to provide a composition comprising one or more cytochalasin derivatives containing an epoxide group, a carbonate group, or both.

It is a yet another object of the present invention to provide a composition comprising one or more cytochalasin or chaetoglobosin.

It is a further object of the present invention to provide new isoindolinone compounds having an epoxide group, a carbonate group, or both.

It is an object of the present invention to provide a composition comprising these isoindolinone derivatives which inhibit angiogenesis.

It is another object of the present invention to provide a method for inhibiting angiogenesis.

It is yet another object of the present invention to provide a composition for inhibiting angiogenesis by oral administration of the composition.

It is a further object of the present invention to provide a method of treating diseases and processes that are mediated by angiogenesis.

It is an object of the present invention to provide a composition for treating or repressing the growth of a cancer.

It is another object of the present invention to provide a therapy for cancer that has minimal side effects.

It is yet another object of the present invention to provide a therapy for neovascularization.

It is a further object of the present invention to provide a method and composition for treating diseases and processes that are mediated by angiogenesis including, but not limited to, Kaposi's sarcoma, hemangioma, solid tumors, blood borne tumors, leukemia, metastasis, telangiectasia, psoriasis, scleroderma, pyogenic granuloma, myocardial angiogenesis, Crohn's disease, plaque neovascularization, coronary collaterals, cerebral collaterals, arteriovenous malformations, ischemic limb angiogenesis, corneal diseases, rubeosis, neovascular glaucoma, diabetic retinopathy, proliferative vitreoretinopathy including those forms not associated with diabetes, retrolental fibroplasia, arthritis, diabetic neovascularization, macular degeneration, wound healing, peptic ulcer, Helicobacter related diseases, fractures, keloids, vasculogenesis, hematopoiesis, ovulation, menstruation, placentation, and cat scratch fever.

These and other objects, features, and advantages of the present invention will become apparent after a review of the following detailed description of the disclosed embodiments and the appended claims.

BRIEF DESCRIPTION OF THE DRAWINGS

FIG. 1 depicts the reaction scheme for preparing isoindolinone derivatives of the present invention.

DETAILED DESCRIPTION OF THE PREFERRED EMBODIMENTS

Figure 2A:
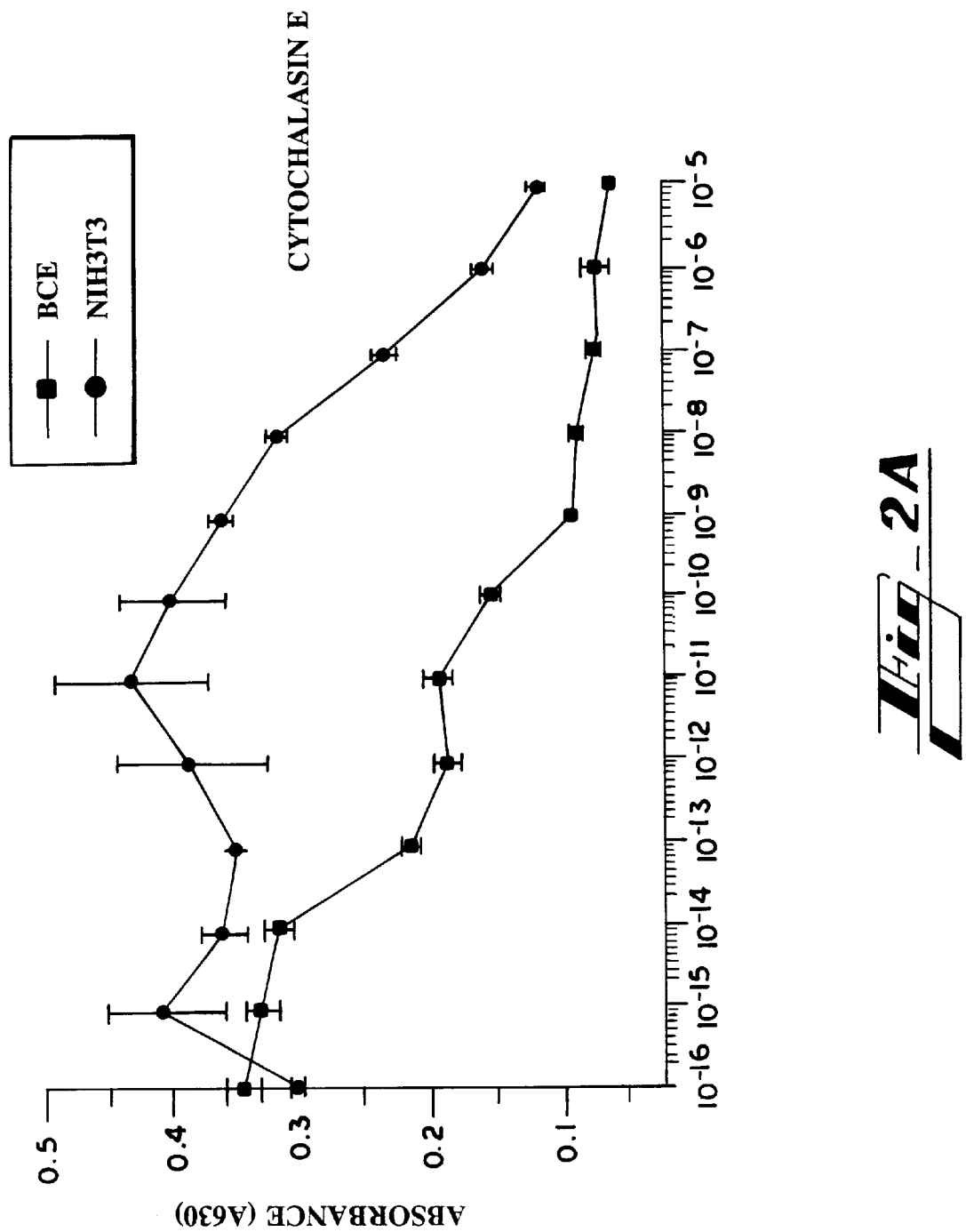
FIGS. 2A–2C depict the inhibition of bovine capillary endothelial cell proliferation (BCE) in Swiss mouse embryo fibroblast cells.

In one aspect, the present invention comprises compositions and methods of inhibiting angiogenesis with cytochalasin derivatives. The present invention also comprises methods of treating angiogenesis dependent and angiogenesis associated diseases by administering a cytochalasin derivative or a composition containing a cytochalasin derivative to a person or animal having such a disease.

The present invention encompasses the use of any cytochalasin derivative. The term "cytochalasin derivative" means any compound having the cytochalasan structure,

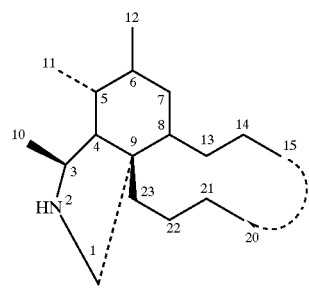

including, but not limited to, Cytochalasins, Chaetoglobulins, Aspochalasins, Zygosporins, and Phomins and derivatives thereof.

Preferred compounds of the invention include cytochalasin derivatives having either an epoxide group, a carbonate group, or both. Several naturally occurring cytochalasin derivatives contain an epoxide group. These include, but not limited to, cytochalasin E ((6S,7S,16R,18R)-6,7-epoxy-18-hydroxy-16-methyl-10-phenyl-21,23-dioxa-[13]cytochalasa-13(E),19(E)-diene-1,17,22-trione), cytochalasin F ((6S,7S,16R,20R)-6,7-epoxy- 20-hydroxy-16-methyl-10-phenyl-24-oxa-[14]cytochalasa-13(E),21(E)-diene-1,23-dione), cytochalasin Q, cytochalasin R, rosellichalasin, and chaetoglobosin A ((6S,7S,16R,19R)-6,7-epoxy-10-(indol-3-yl)-19-hydroxy-16,18-dimethyl-[13]cytochalasa-13(E),17(E),21(E)-triene-1,20,23-trione), chaetoglobosin C ((6S,7S,16S)-6,7-epoxy-10-(indol-3-yl)-16,18-dimethyl-[13]cytochalasa-13(E),17(E)-diene-1,19,20,23-tetraone), chaetoglobosin F ((6S,7S,16R)-6,7-epoxy-20-hydroxy-10-(indol-3-yl)-16,18-dimethyl-[13]cytochalasa-13(E),17(E)-diene-1,19,23-trione), and chaetoglobosin K.

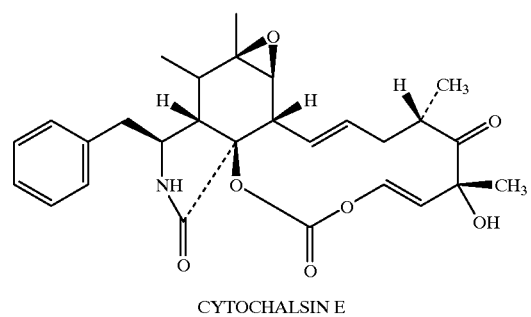

CYTOCHALSIN E

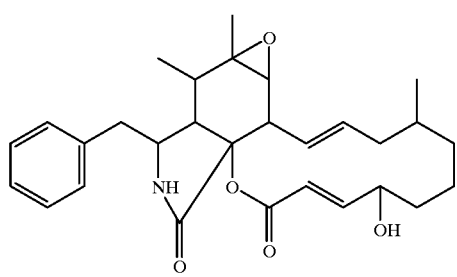
CYTOCHALASIN F

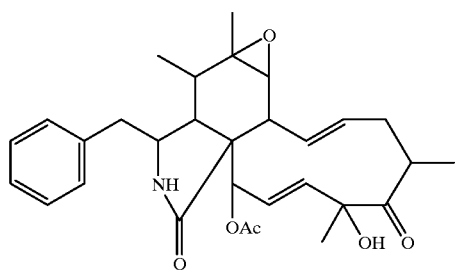
CYTOCHALASIN Q

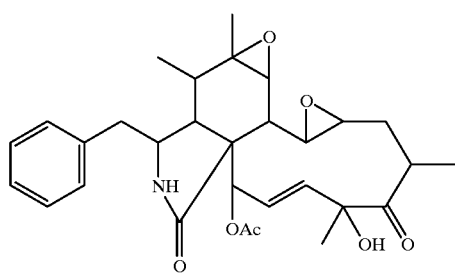
CYTOCHALASIN R

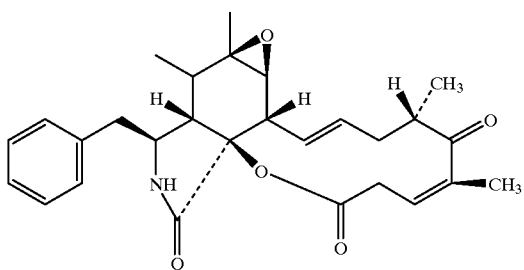
ROSELLICHALASIN

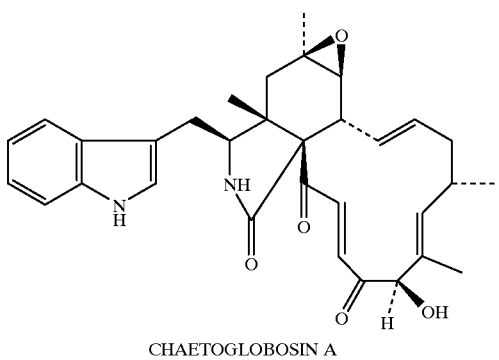
CHAETOGLOBOSIN A

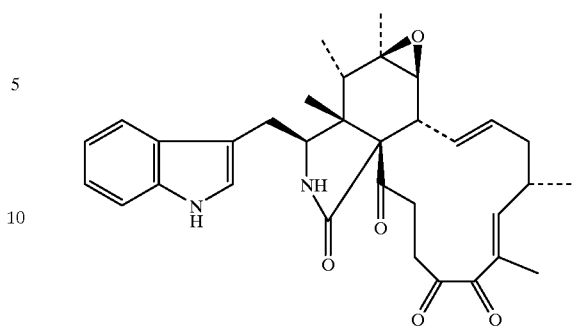
CHAETOGLOBOSIN C

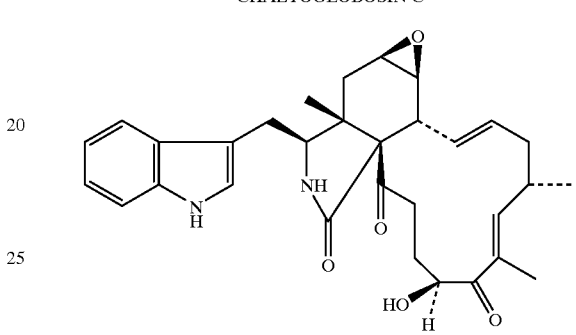
CHAETOGLOBOSIN F

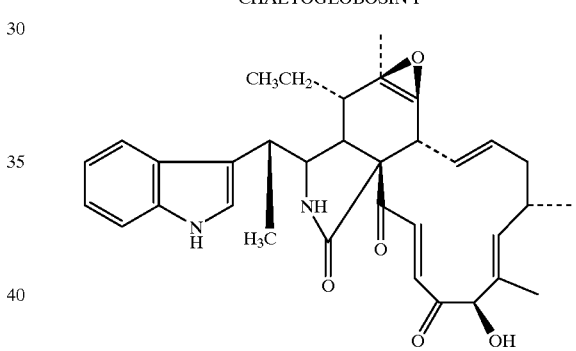
CHAETOGLOBOSIN K

The cytochalasins of the invention can be produced by fermentation from molds or fungi by methods known in the prior art. For example, cytochalasin E is a metabolite of both *Rosellinia necatrix* and *Aspergillus clavatus* (Aldridge, et al., *J. Chem. Soc.* (D), *Chem. Comm.*, 148–49 (1972)), and cytochalasin D is a metabolite of *Zygosporium masonii* (Vederas and Tamm, Helv. Chim. Acta, 59: 558–66 (1976)).

The present invention also comprises derivatives of these compounds which retain an epoxide group, a carbonate group, or both, such as 17-hydroxy-cytochalasin E, 19,20-dihydro-cytochalasin E, reduction products of cytochalasin E, and the corresponding derivatives of other cytochalasins. Examples of these compounds include, but are not limited to, the following:

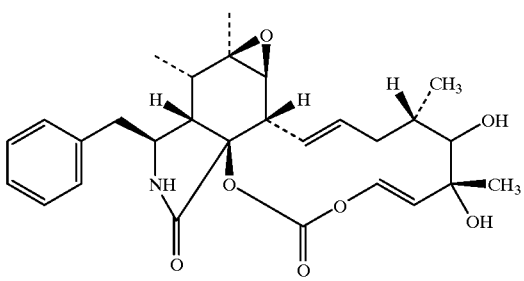

17-HYDROXYCYTOCHALASIN E

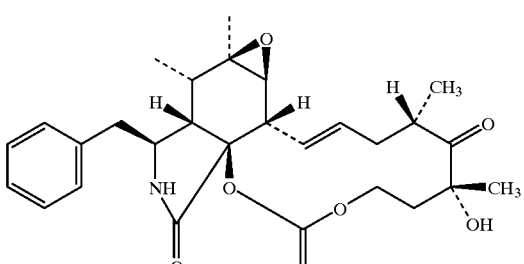

19, 20-DIHYDROCYTOCHALASIN E

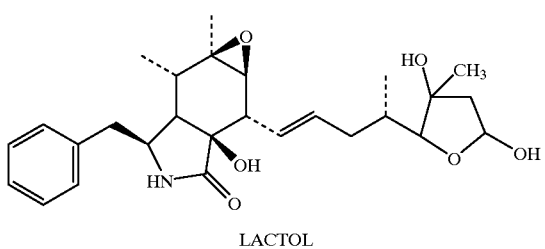

LACTOL

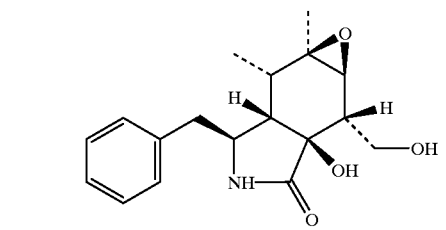

OZONOLYSIS ANALOG OF CYTOCHALASIN E

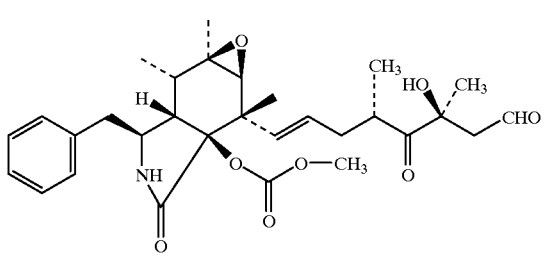

ALDEHYDE METHYL ESTER OF CYTOCHALASIN E

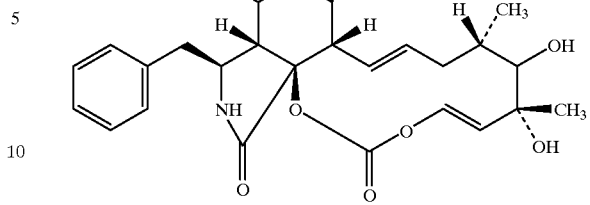

17-OH-DIHYDRO CYTOCHALASIN E

These compounds can be produced by methods known in the art; for example, those methods described in Steyn, et al. *J. Chem. Soc. Perkins Trans.* 1, 541–44 (1982) and Aldridge, et al., *J. Chem. Soc. Chem. Comm.*, 551–52 (1973).

Other cytochalasin compounds, although not naturally containing an epoxide group, can be modified to contain an epoxide group. For example, an epoxide group can be formed on cytochalasin derivatives having a methyl group attached to the benzene portion of the isoindolinone ring through reaction with a peroxide.

The present inventors have found that inhibition of angiogenesis is greater in cytochalasin compounds having an epoxide group and/or a carbonate group, such as cytochalasin E. In another aspect, the present invention comprises new isoindolinone derivatives having an epoxide group, a carbonate group, or both. These compounds lack the macrocyclic ring of the cytochalasin derivatives and have the following generic formula:

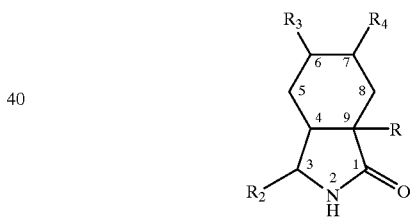

wherein

R is H, OH, $OR_1$, wherein $R_1$ is H, alkyl, aryl, $C(O)$—$R_1$, or $C(O)OR_1$; $R_2$ is H, alkyl, aryl, heteroaryl, aralkyl, or heteroaralkyl; $R_3$ is =$CH_2$, H, $CH_3$; $R_4$ is H, OH, or $OR_1$;

and where there is optionally an exocyclic epoxide ring between C6 and C7, provided that the compound contains at least one epoxide or carbonate group.

Aryl includes moieties having a 5 to 12 membered ring system, for example phenyl and napthyl. Aralkyl include moieties having a 5 to 12 membered ring system and a straight or branched alkyl chain of 1 to 8 carbon atoms, for example benzyl. Heteroaryl includes moieties having a 6 to 12 membered ring system containing from 1 to 3 heterocyclic atoms selected from N, O, and S. Heteroaralkyl includes moieties having a 6 to 12 membered ring system containing from 1 to 3 heterocyclic atoms selected from N, O, and S and a straight or branched alkyl chain of 1 to 8 carbon atoms. Each of the above identified substituents may be substituted or unsubstituted.

Particularly preferred compounds of the present invention include the following:

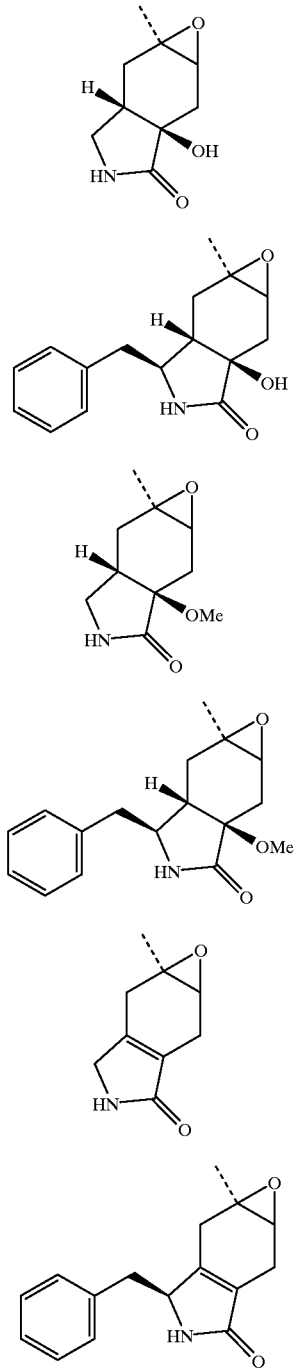

-continued

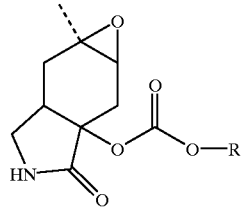

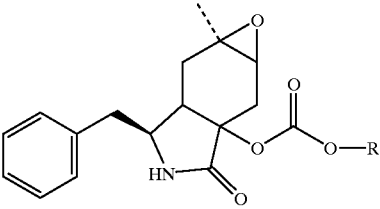

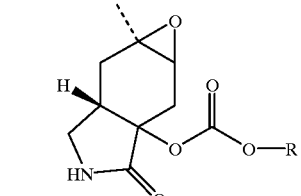

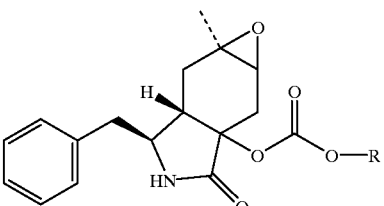

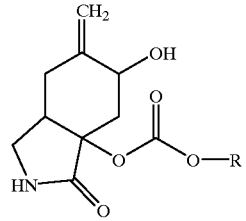

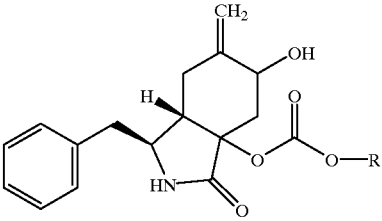

These compounds have lower cytotoxicity than the cytochalasins due to the absence of the macrocyclic ring structure, allowing higher doses of the compounds to be administered without adverse effects. These isoindolinone derivatives also possess greater angiogenesis inhibitory activity than the cytochalasins, allowing smaller doses to achieve the same inhibitory activity.

The isoindolinone derivatives of the present invention can be produced from 6-methyl-isoindol-1,3-dione. (FIG. 1) The 6-methyl-isoindol-1,3-dione first undergoes a reduction of the oxo group. This reduction may be metal catalyzed, for example, by zinc. Next, the intermediate is optionally alkylated at the 3-position, for example, with n-butyl lithium and benzyl bromide.

For those compounds containing an epoxide ring, the epoxide ring is formed in two steps. First, a 6-methyl-isoindol-1,3-dione derivative is reacted with a 1:1 ratio of tetrahydrofuran (THF) and tert-butyl alcohol in liquid ammonia. Next, the intermediate is reacted with a peroxy acid. The 6-methyl-isoindol-1,3-dione derivative can be carbonated by hydroboration followed by oxidation.

The present invention also comprises compositions and methods of inhibiting angiogenesis with such isoindolinone derivatives. The invention further comprises methods of treating angiogenesis dependent and angiogenesis associated diseases by administering an isoindolinone derivative or a composition containing a isoindolinone derivative to a person or animal having such a disease.

The cytochalasin and isoindolinone derivatives described above can be provided as pharmaceutically acceptable compositions using formulation methods known to those of ordinary skill in the art. These formulations can be administered by standard routes. In general, the pharmaceutical compositions of the present invention can be administered by topical, transdermal, oral, rectal or parenteral (e.g., intravenous, subcutaneous or intramuscular) routes. In addition, the compositions can be incorporated into biodegradable polymers allowing for sustained release of the compound, the polymers being implanted near the desired site of drug delivery, for example, at the site of a tumor. Such biodegradable polymers and their use for delivery of pharmaceuticals are known in the art. (e.g., Brem et al., J. Neurosurg. 74:441–46 (1991)).

The dosage of the compound will depend on the condition being treated, the particular compound, and other clinical factors such as the weight and condition of the human or animal to be treated and the chosen route of administration. It is to be understood that the present invention has application for both human and veterinary use. In one embodiment, the cytochalasin derivatives of the present invention can be administered to humans at a dose between approximately 0.01 mg/kg body weight per day and approximately 100 mg/kg body weight per day. The preferred dosage of cytochalasin derivatives is approximately 2 mg/kg/day. The isoindolinone derivatives of the present invention can be administered at similar dosages.

The pharmaceutical compositions of the present invention include those suitable for oral, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s). In general, the formulations are prepared by uniformly and intimately bringing into associate the active ingredient with liquid carriers or finely divided solid carriers or both, and then, if necessary, shaping the product.

Formulations of the present invention suitable for oral administration may be presented as discrete units such as capsules, cachets, or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels, and pastes comprising the ingredient to be administered in a pharmaceutical acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats, and solutes which render the formulation isotonic with the blood of the intended recipient and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

Diseases associated with corneal neovascularization that can be treated according to the present invention include but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, mariginal keratolysis, trauma, rheumatoid arthritis, systemic lupus, polyarteritis, Wegener's sarcoidosis, scleritis, Stevens-Johnson disease, pemphigoid radial keratotomy, and corneal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, Eales' disease, Behcet's disease, infections causing a retinitis or choroiditis, presumed ocular histoplasmosis, Bests disease, myopia, optic pits, Stargardt's disease, pars planitis, chronic retinal detachment, hyperviscosity syndromes, toxoplasmosis, trauma and post-laser complications. Other diseases include, but are not limited to, diseases associated with rubeosis (neovasculariation of the angle) and diseases caused by the abnormal proliferation of fibrovascular or fibrous tissue including all forms of proliferative vitreoretinopathy, whether or not associated with diabetes.

Diseases associated with chronic inflammation can be treated by the compositions and methods of the present invention. Diseases with symptoms of chronic inflammation include inflammatory bowel diseases such as Crohn's disease, ulcerative colitis, psoriasis, sarcoidosis and rheumatoid arthritis. Angiogenesis is a key element that these chronic inflammatory diseases have in common. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis by the compositions and methods of the present invention inhibit the formation of the granulomas and alleviate the disease.

The compositions and methods of the present invention can be used to treat patients with inflammatory bowel diseases such as Crohn's disease and ulcerative colitis. Both Crohn's disease and ulcerative colitis are characterized by chronic inflammation and angiogenesis at various sites in the gastrointestinal tract. Crohn's disease is characterized by chronic granulomatous inflammation throughout the gastrointestinal tract consisting of new capillary sprouts surrounded by a cylinder of inflammatory cells. Inhibition of angiogenesis by the compositions and methods of the present invention inhibits the formation of the sprouts and prevents the formation of granulomas.

Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea.

The inflammatory bowel diseases also show extraintestinal manifestations such as skin lesions. Such lesions are characterized by inflammation and angiogenesis and can occur at many sites other than the gastrointestinal tract. The compositions and methods of the present invention are also capable of treating these lesions by preventing the angiogenesis, thus reducing the influx of inflammatory cells and the lesion formation.

Sarcoidosis is another chronic inflammatory disease that is characterized as a multisystem granulomatous disorder. The granulomas of this disease may form anywhere in the body and thus the symptoms depend on the site of the granulomas and whether the disease active. The granulomas are created by the angiogenic capillary sprouts providing a constant supply of inflammatory cells.

The compositions and methods of the present invention can also treat the chronic inflammatory conditions associated with psoriasis. Psoriasis, a skin disease, is another chronic and recurrent disease that is characterized by papules and plaques of various sizes. Prevention of the formation of the new blood vessels necessary to maintain the characteristic lesions leads to relief from the symptoms.

Another disease which can be treated according to the present invention is rheumatoid arthritis. Rheumatoid arthritis is a chronic inflammatory disease characterized by nonspecific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Other diseases that can be treated according to the present invention are hemangiomas, Osler-Weber-Rendu disease, or hereditary hemorrhagic telangiectasia, solid or blood borne tumors and acquired immune deficiency syndrome. In particular, the invention is useful for treating cancers, including, but not limited to, those cancers exhibiting solid tumors, such as breast, lung, ovarian, testicular, and colon cancers This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Bovine capillary endothelial (BCE) cells and Swiss mouse embryo fibroblast cells (NIH3T3) were isolated as previously described (Folkman, , et al., *Proc. Nat. Acad. Sci USA.*, 76:5217–21 (1979)) and maintained in DMEM supplemented with 10% heat-inactivated bovine calf serum (BCS), antibiotics, and 3 ng/ml recombinant human bFGF (Scios Nova, Mountainview, Calif.). Monolayers of the cells growing in 6-well plates were dispersed in a 0.05% trypsin solution. The cells were re-suspended with DMEM containing 10% BCS. Approximately 12,500 cells in 0.5 ml were added to each well of gelatinized 24-well tissue culture plates and incubated at 37° C. (in 10% $CO_2$) for 24 hours. The medium was replaced with 500 ml of fresh DMEM containing 5% BCS. Samples of cytochalasin E, cytochalasin A, and cytochalasin H were added to each well in triplicate. After 30 minutes of incubation, bFGF was added to a final concentration of 1 ng/ml. After 72 hours of incubation, cells were trypsinized, re-suspended in Hematall (Fisher Scientific, Pittsburg, Pa.) and counted with a Coulter counter.

Figure 2B:
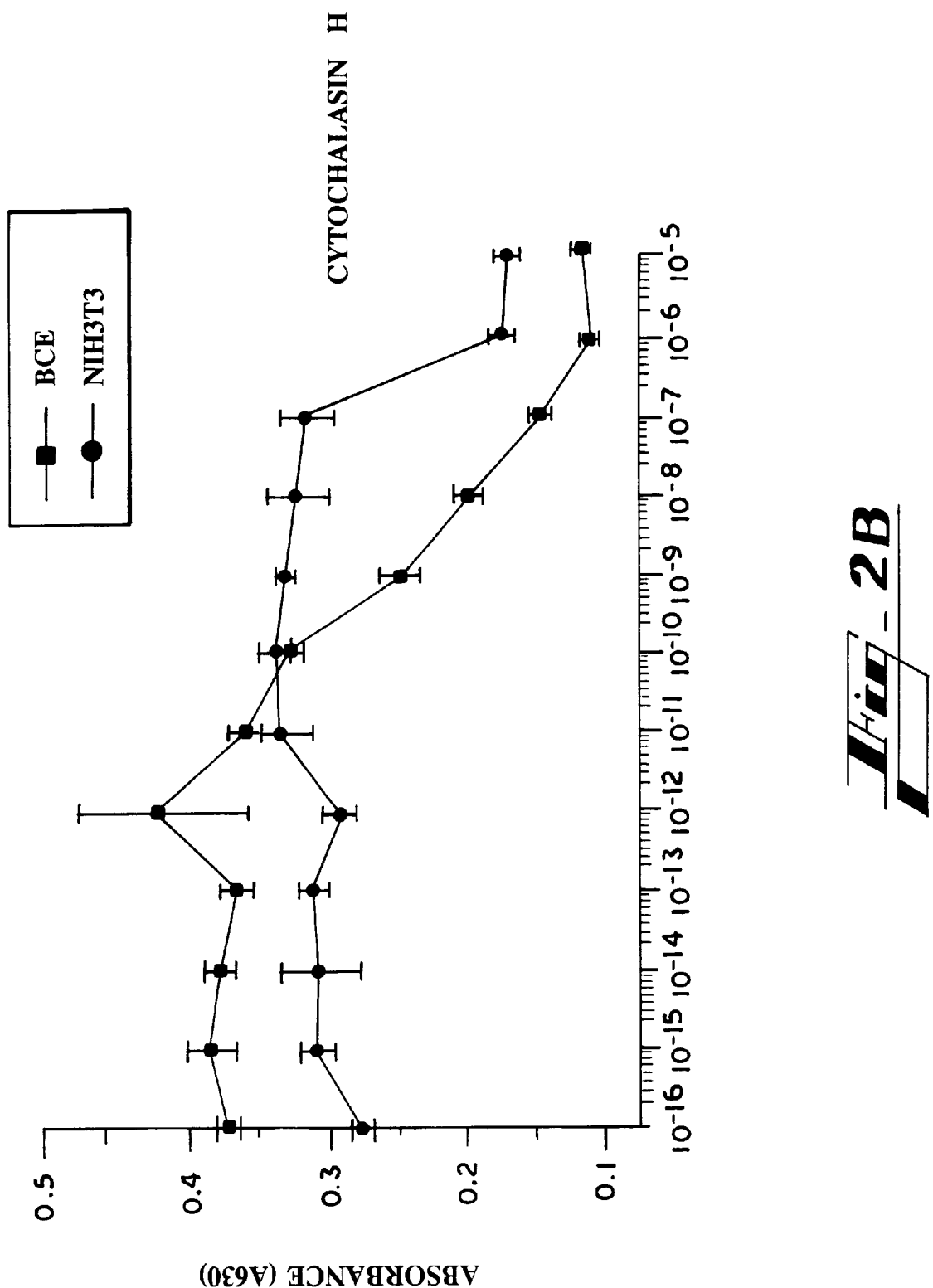
Figure 2C:
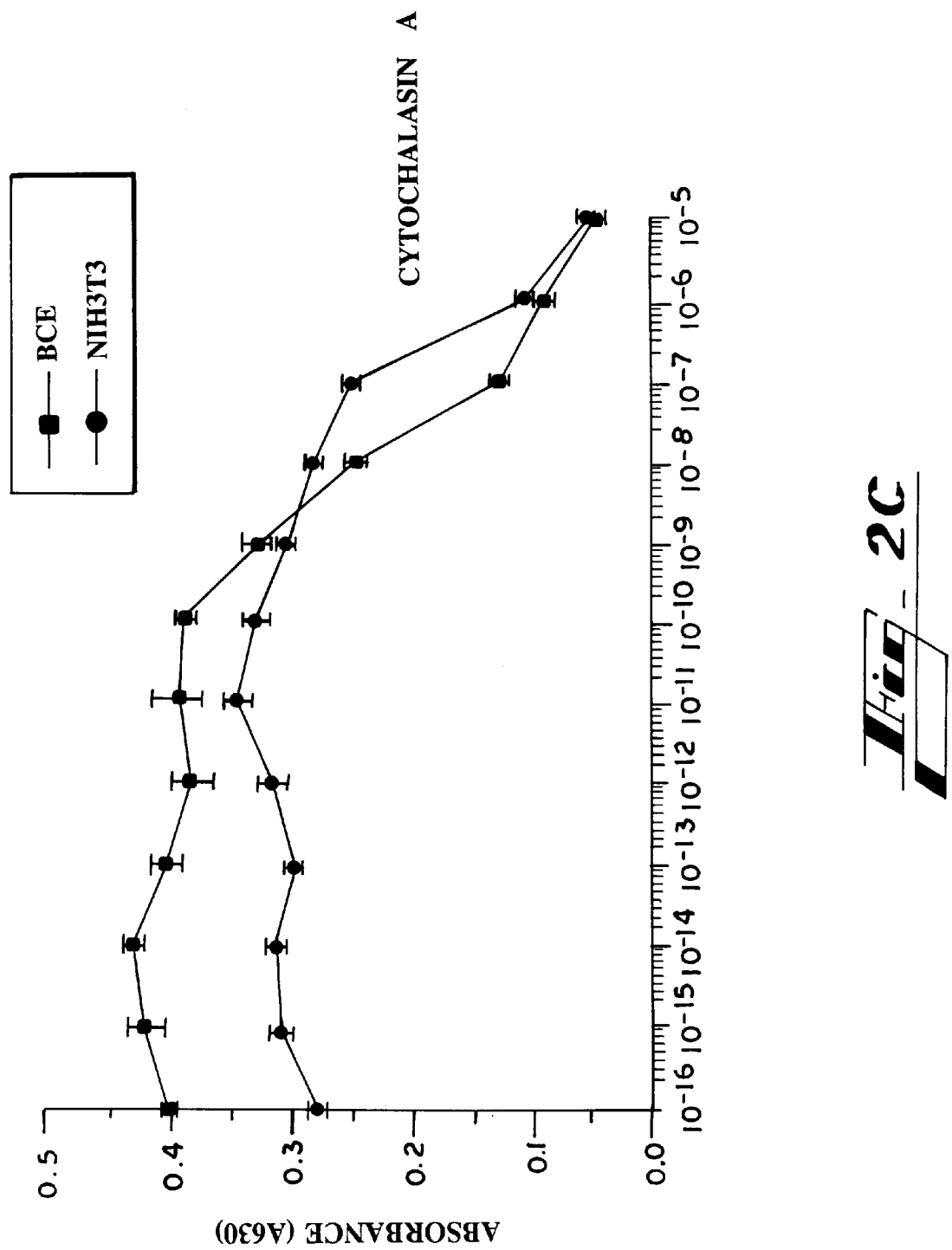

The results are shown in FIG. 2. FIG. 2 is a graph showing the inhibition of bovine capillary endothelial cell proliferation (BCE) (squares) compared to Swiss mouse embryo fibroblast cells (NIH3T3). The abscissa shows absorbance at 630 Angstroms by stained cell nuclei, which corresponds to cell number. The ordinate measures drug concentration in grams per milliliter. FIG. 2A shows the administration of cytochalasin E; FIG. 2B shows the administration of cytochalasin H, and the FIG. 2C shows the administration of cytochalasin A.

The results show that cytochalasin E inhibits endothelial cell proliferation with an $IC_{50}$ of 2 pm/ml, and is 40,000/1 selective for endothelial cells over fibroblast cells. The other two cytochalasins, cytochalasin H and cytochalasin A, which lack epoxide moieties, are 1000-fold less active.

Example 2

Bovine capillary endothelial (BCE) were isolated as previously described (Folkman, , et al., *Proc. Nat. Acad. Sci USA.*, 76:5217–21 (1979)) and maintained in DMEM supplemented with 10% heat-inactivated bovine calf serum (BCS), antibiotics, and 3 ng/ml recombinant human bFGF (Scios Nova, Mountainview, Calif.). Monolayers of the cells growing in 6-well plates were dispersed in a 0.05% trypsin solution. The cells were re-suspended with DMEM containing 10% BCS. Approximately 12,500 cells in 0.5 ml were added to each well of gelatinized 24-well tissue culture plates and incubated at 37° C. (in 10% $CO_2$) for 24 hours. The medium was replaced with 500 ml of fresh DMEM containing 5% BCS. Samples of cytochalasin E and epoxycytochalasin J were added to each well in triplicate. After 30 minutes of incubation, bFGF was added to a final concentration of 1 ng/ml. After 72 hours of incubation, cells were trypsinized, re-suspended in Hematall (Fisher Scientific, Pittsburg, Pa.) and counted with a Coulter counter.

Figure 3:
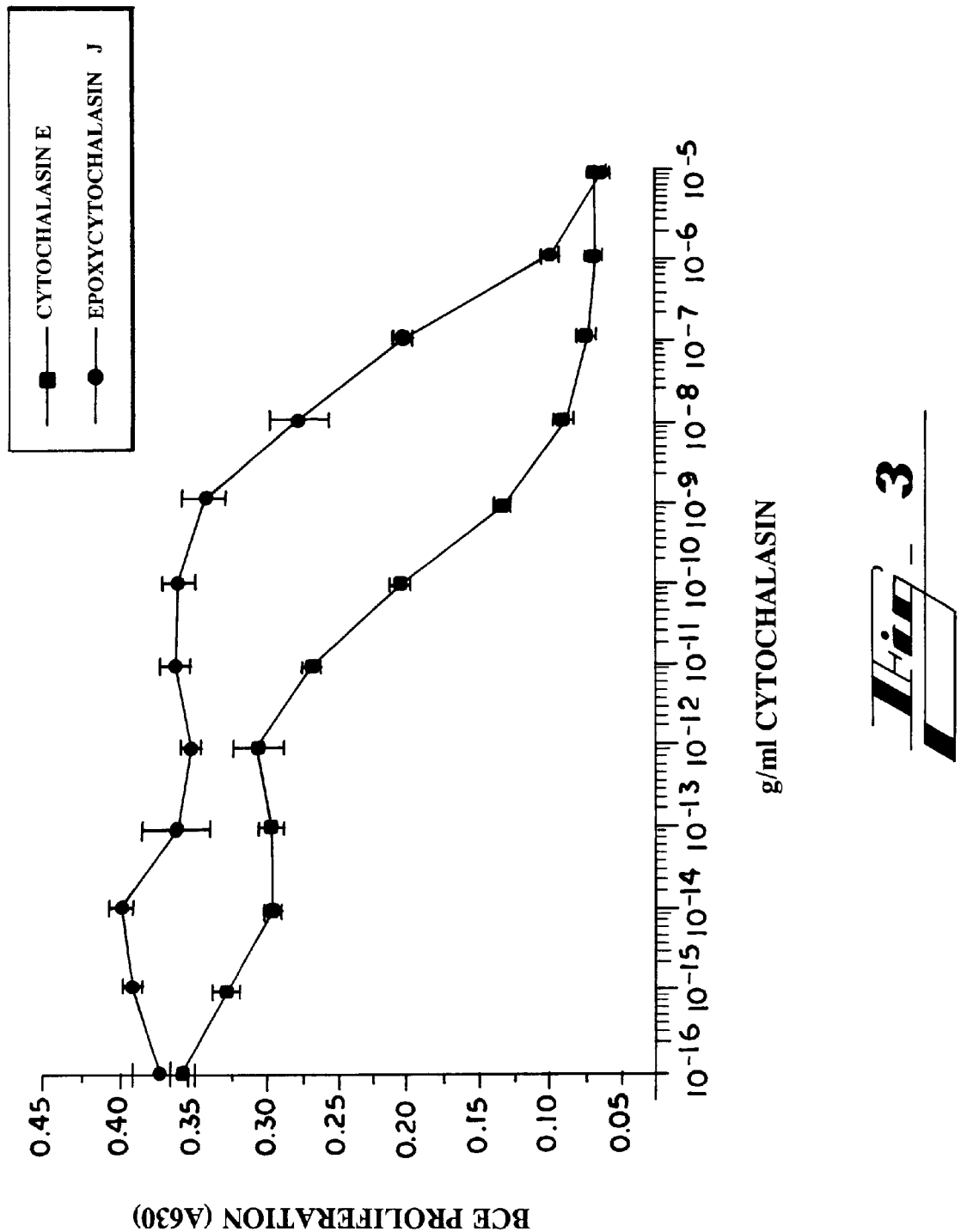
FIG. 3 compares the activity of cytochalasin E and epoxycytochalasin J in the inhibition of bovine capillary endothelial cell proliferation (BCE).

The results are shown in FIG. 3. FIG. 3 shows that epoxycytochalasin J is an even more effective inhibitor of bovine capillary endothelial cell proliferation (BCE) (squares) than cytochalasin E. The abscissa shows absorbance at 630 Angstroms by stained cell nuclei, which corresponds to cell number. The ordinate measures drug concentration in grams per milliliter.

Example 3

Pellets for implantation into rabbit corneas were made by mixing 110 $\mu$l of saline containing 12 $\mu$g of recombinant bFGF (Takeda Pharmaceuticals-Japan) with 40 mg of sucralfate (Bukh Meditec-Denmark); this suspension was added to 80 $\mu$l of 12% hydron (Interferon Sciences) in ethanol. 10 $\mu$l aliquots of this mixture was then pipetted onto teflon pegs and allowed to dry producing approximately 17 pellets. A pellet was implanted into corneal micropockets of each eye of an anesthetized female New Zealand white rabbit, 2 mm from the limbus followed by topical application of erythromycin ointment onto the surface of the cornea. The animals were fed daily from 2 days post-implantation by gastric lavage with cytochalasin E or the aldehyde methyl ester derivative of cytochalasin E suspended in 0.5% carboxymethyl cellulose or 0.5% carboxymethyl cellulose alone. The animals were examined with a slit lamp every other day in a masked manner by the same corneal specialist. The area of corneal neovascularization was determined by measuring with a reticule the vessel length (L) from the limbus and the number of clock hours (C) of limbus involved. A formula was used to determine the area of a circular band segment: $C/12 * 3.1416 [r^2-(r-L)^2]$ where r=6 mm the measured radius of the rabbit cornea. Various mathematical models were utilized to determine the amount of vascularized cornea and this formula was found to provide the most accurate approximation of the area of the band of neovascularization that grows towards the pellet.

It is important to note that the rabbit cornea assay is preferable because it will generally recognize compounds that are inactive per se but are metabolized to yield active compounds.

It was found that subcutaneously administered cytochalasin E at a dosage of 2 mg/kg/day inhibits basic fibroblast growth factor (bFGF) driven corneal neovascularization by 50% and that the aldehyde methyl ester derivative of cytochalasin E at a dosage of 2 mg/kg/day inhibits bFGF driven corneal neovascularization by 38%.

Example 4

The neovascularization experiment described in Example 2 was repeated using the corneal micropockets in mice. The compounds tested were cytochalasin E, astaphiatin, arglabin, epoxycytochalasin-H, ozonolyzed cytochalasin-E, and precursor cytochalasin-E. The results of these compound's ability to inhibit angiogenesis are shown in Table 1.

TABLE 1

| Compound | % Inhibition | % Weight Loss |
| --- | --- | --- |
| Cytochalasin-E | 45.00 | 0.00 |
| Astaphiatin | 33.56 | 6.92 |
| Arglabin | 22.72 | 2.69 |
| Epoxycytochalasin-H | 27.35 | 2.46 |
| Ozonolyzed Cytochalasin-E (JHS 199) | 20.00 | 4.00 |
| Precursor Cytochalasin-E (JHS-F6P2) | 20.00 | 2.50 |

Example 5

By screening a variety of murine tumors capable of inhibiting their own metastases, a Lewis lung carcinoma was selected in which the primary tumor most efficiently inhibited lung metastasis. Syngeneic C57Bl6/J six-week-old male mice were injected (subcutaneous dorsum) with $1 \times 10^6$ tumor cells. Visible tumors first appeared after 3–4 days. When tumors were approximately 1500 $mm^3$ in size, mice were randomized into two groups. The primary tumor was completely excised in the first group and left intact in the second group after a sham operation. Although tumors from 500 $mm^3$ to 3000 $mm^3$ inhibited growth of metastases, 1500 $mm^3$ was the largest primary tumor that could be safely resected with high survival and no local recurrence.

After 21 days, all mice were sacrificed and autopsied. In mice with an intact primary tumor, there were four +2 visible metastases, compared to fifty +5 metastases in the mice in which the tumor had been removed (p<0.0001). These data were confirmed by lung weight, which correlates closely with tumor burden, as has been previously demonstrated. There was a 400% increase in wet lung weight in the mice that had their tumors removed compared to mice in which the tumor remained intact (p<0.0001).

This experimental model gave reproducible data and the experiment described is reproducible. This tumor is labeled "Lewis lung carcinoma—low metastatic" (LLC—Low). The tumor also suppressed metastases in a nearly identical pattern in SCID mice, which are deficient in both B and T lymphocytes.

It was found that 2 mg/kg/day of cytochalasin E inhibited tumor growth by 74%. In the same model, it was found that 2 mg/kg/day of the aldehyde methyl ester derivative of cytochalasin E inhibited tumor growth by 30%.

Example 6

The Lewis lung experiment of Example 5 was repeated using cytochalasin E and methanolyzed cytochalasin E. The results of this experiment are presented in the table below.

| Inhibition of Tumor Growth | | |
|---|---|---|
| Compound | Dose | T/C |
| Cytochalasin-E | 2.0 mg/kg qd | 0.28 |
| Methanolyzed Cytochalasin-E | 2.0 mg/kg od | 0.70 |

The above examples are intended to be demonstrative, rather than limiting, of the embodiments contemplated by the invention and encompassed within the scope of the claims.

We claim:

1. A method of inhibiting angiogenesis in a human or animal comprising administering to the human or animal an angiogenesis inhibitory amount of a composition comprising a cytochalasin derivative.

2. The method of claim 1 wherein the cytochalasin derivative possesses an epoxide group, a carbonate group, or both.

3. The method of claim 1 wherein the cytochalasin derivative is selected from the group consisting of cytochalasin A, cytochalasin B, cytochalasin C, cytochalasin D, cytochalasin F, cytochalasin H, cytochalasin J, cytochalasin K, cytochalasin Q, cytochalasin R, rosellichalasin, epoxycytochalasin H, epoxycytochalasin J, chaetoglobosin A, chaetoglobosin C, chaetoglobosin F, and chaetoglobosin K.

4. The method of claim 1 wherein the cytochalasin derivative is selected from the group consisting of astaphiatin, arglabin, ozonolyzed cytochalasin E, methanolyzed cytochalasin E, aldehyde methyl ester of cytochalasin E, 17-hydroxycytochalasin E, 19,20-dihydrocytochalasin E, and rearranged cytochalasin E.

5. A method of treating an angiogenesis-associated or angiogenesis-dependent disease in a human or animal comprising administering to the human or animal an angiogenesis inhibiting amount of a cytochalasin derivative.

6. The method of claim 5 wherein the cytochalasin derivative possesses an epoxide group, a carbonate group, or both.

7. The method of claim 5 wherein the cytochalasin derivative is selected from the group consisting of cytochalasin A, cytochalasin B, cytochalasin C, cytochalasin D, cytochalasin F, cytochalasin H, cytochalasin J, cytochalasin K, cytochalasin Q, cytochalasin R, rosellichalasin, epoxycytochalasin H, epoxycytochalasin J, chaetoglobosin A, chaetoglobosin C, chaetoglobosin F, and chaetoglobosin K.

8. The method of claim 5 wherein the cytochalasin derivative is selected from the group consisting of astaphiatin, argiabin, ozonolyzed cytochalasin E, methanolyzed cytochalasin E, aldehyde methyl ester of cytochalasin E, 17-hydroxycytochalasin E, 19,20-dihydrocytochalasin E, and rearranged cytochalasin E.

9. A compound having the formula

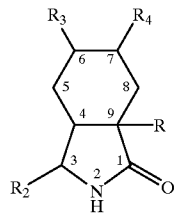

wherein

R is H, OH, $OR_1$, wherein $R_1$ is H, alkyl, aryl, COH, C(O)-alkyl, C(O)-aryl, C(O)OH, C(O)O-alkyl, C(O)O-aryl $R_2$ is H, alkyl, aryl, heteroaryl, aralkyl, or heteroaralkyl;

$R_3$ is $=CH_2$, H, $CH_3$;

$R_4$ is H, OH, or $OR_1$;

and where there is optionally an exocyclic epoxide ring between C6 and C7, provided that the compound contains at least one epoxide or carbonate group.

10. The compound of claim 9 wherein aryl is a substituted or unsubstituted 5 to 12 membered aromatic ring system;

aralkyl is a substituted or unsubstituted 5 to 12 membered aromatic ring system attached through a straight or branched alkyl chain of 1 to 8 carbon atoms;

heteroaryl is a substituted or unsubstituted 6 to 12 membered heteroaromatic ring system containing from 1 to 3 heterocyclic atoms selected from N, O, and S; and heteroaralkyl is a substituted or unsubstituted 6 to 12 membered heteroaromatic ring system containing from 1 to 3 heterocyclic atoms selected from N, O, and S attached through a straight or branched alkyl chain 1 to 8 carbon atoms.

11. The compound of claim 9 selected from the group of

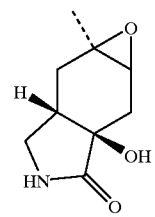

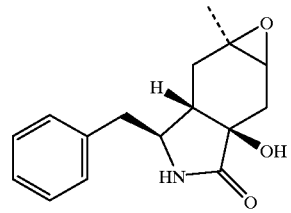

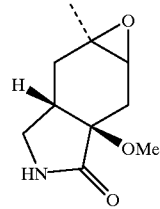

-continued

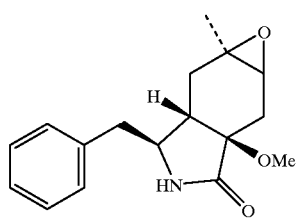
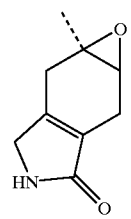
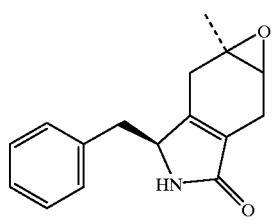
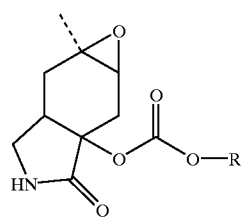
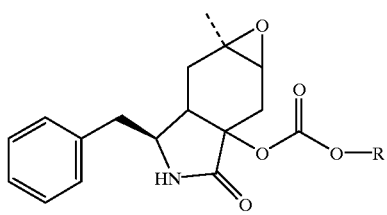
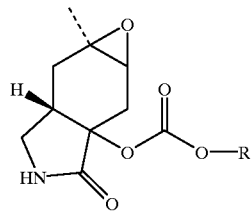
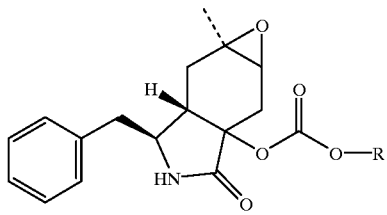

-continued

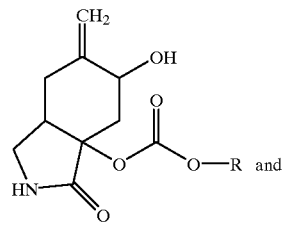
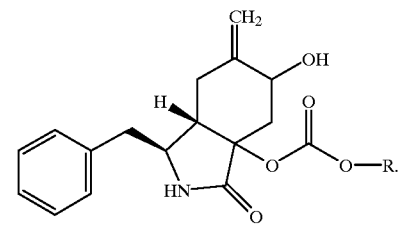

12. A method of inhibiting angiogenesis in a human or animal comprising administering to the human or animal an angiogenesis inhibitory amount of a composition comprising a compound having the formula

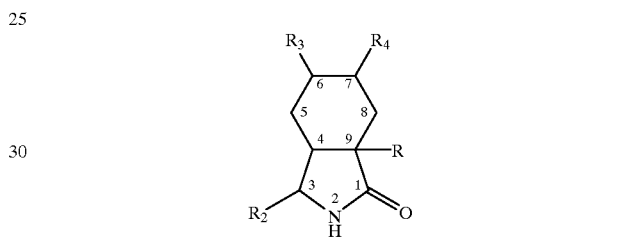

wherein

R is H, OH, $OR_1$, wherein $R_1$ is H, alkyl, aryl, COH, C(O)-alkyl, C(O)-aryl, C(O)OH, C(O)O-alkyl, C(O)O-aryl $R_2$ is H, alkyl, aryl, heteroaryl, aralkyl, or heteroaralkyl;

$R_3$ is $=CH_2$, H, $CH_3$;

$R_4$ is H, OH, or $OR_1$;

and where there is optionally an exocyclic epoxide ring between C6 and C7, provided that the compound contains at least one epoxide or carbonate group.

13. The method of claim 12 wherein the composition comprises a compound selected from the group consisting of

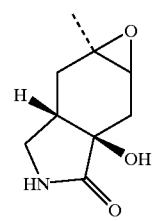
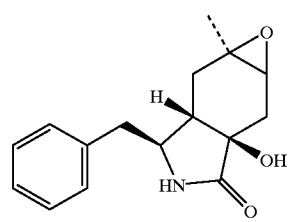

-continued

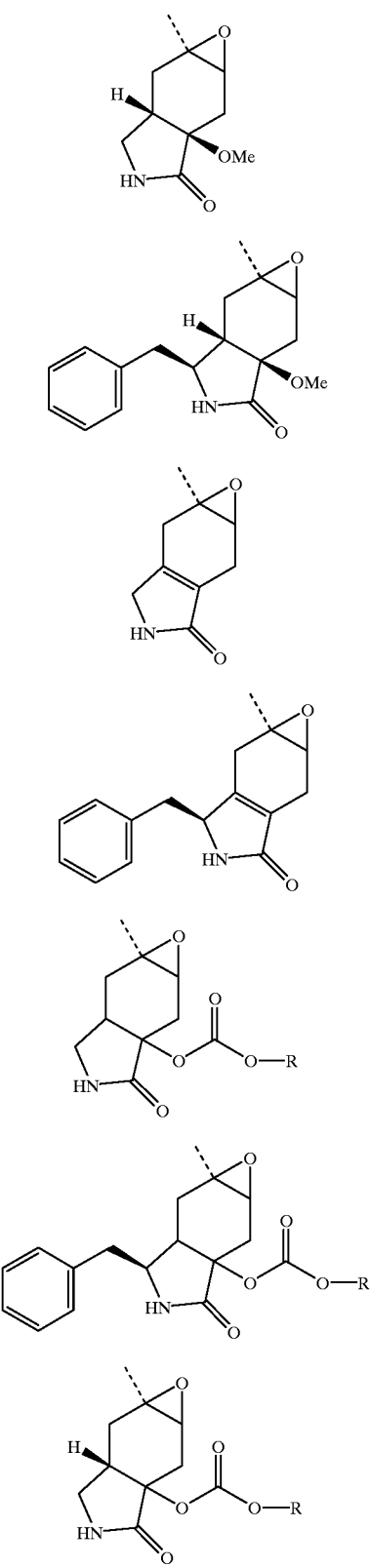

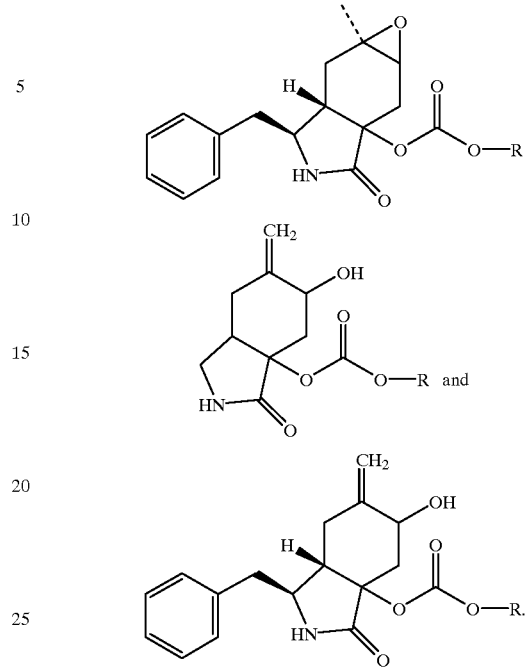

14. A method of treating an angiogenesis-associated or anglogenesis-dependent disease in a human or animal comprising administering to the human or animal an anglogenesis inhibiting amount of a compound of the formula

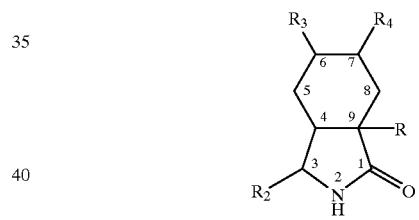

wherein

R is H, OH, $OR_1$, wherein $R_1$ is H, alkyl, aryl, COH, C(O)-alkyl, C(O)-aryl, C(O)OH, C(O)O-alkyl, C(O)O-aryl $R_2$ is H, alkyl, aryl, heteroaryl, aralkyl, or heteroaralkyl;

$R_3$ is =$CH_2$, H, $CH_3$;

$R_4$ is OH, or $OR_1$;

and where there is optionally an exocyclic epoxide ring between C6 and C7, provided that the compound contains at least one epoxide or carbonate group.

15. The method of claim 14 wherein the composition comprises a compound selected from the group consisting of

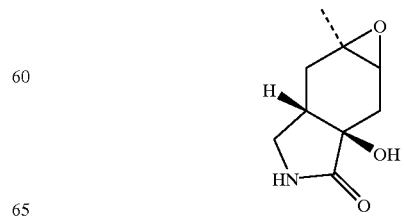

29
-continued
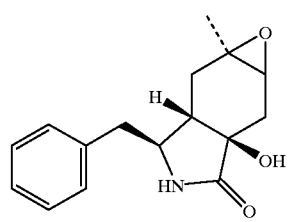
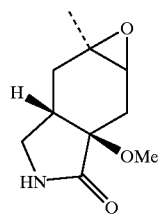
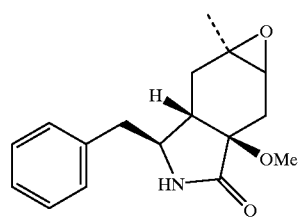
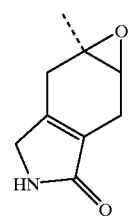
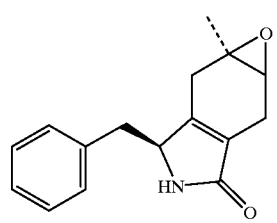
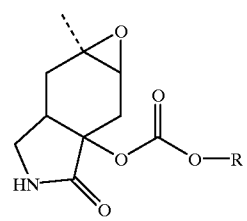
30
-continued
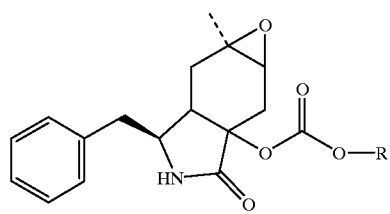
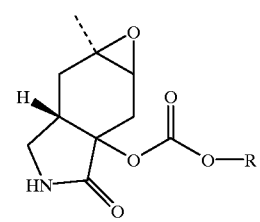
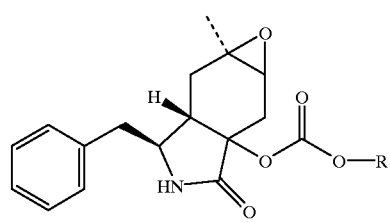
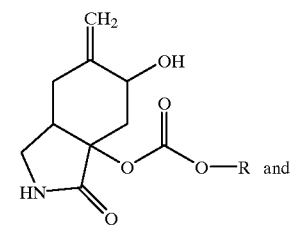
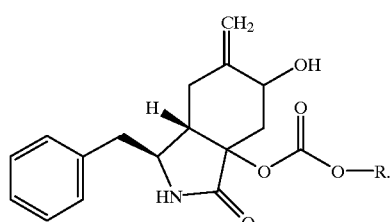
\* \* \* \* \*